(12) United States Patent
Du et al.

(10) Patent No.: US 11,826,205 B2
(45) Date of Patent: *Nov. 28, 2023

(54) ULTRASOUND IMAGING METHOD AND SYSTEM

(71) Applicant: SHENZHEN MINDRAY BIO-MEDICAL ELECTRONICS CO., LTD., Shenzhen (CN)

(72) Inventors: Yigang Du, Shenzhen (CN); Rui Fan, Shenzhen (CN); Yong Li, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 142 days.

This patent is subject to a terminal disclaimer.

(21) Appl. No.: 17/683,505

(22) Filed: Mar. 1, 2022

(65) Prior Publication Data

US 2022/0233173 A1    Jul. 28, 2022

Related U.S. Application Data

(63) Continuation of application No. 15/362,553, filed on Nov. 28, 2016, now Pat. No. 11,259,784, which is a
(Continued)

(51) Int. Cl.
*A61B 8/08*    (2006.01)
*A61B 8/00*    (2006.01)
(Continued)

(52) U.S. Cl.
CPC ............. *A61B 8/5246* (2013.01); *A61B 8/00* (2013.01); *A61B 8/14* (2013.01); *A61B 8/4483* (2013.01);
(Continued)

(58) Field of Classification Search
CPC ..... A61B 8/5246; A61B 8/5223; A61B 8/461; A61B 8/4483; A61B 8/14; A61B 8/00
(Continued)

(56) References Cited

U.S. PATENT DOCUMENTS

| 4,182,173 A | 1/1980 | Papadofrangakis |
| 4,768,515 A | 9/1988 | Namekawa |

(Continued)

FOREIGN PATENT DOCUMENTS

| CN | 101919711 A | 12/2010 |
| CN | 102342848 A | 2/2012 |
| EP | 2628449 A2 | 2/2013 |

*Primary Examiner* — Joseph M Santos Rodriguez
*Assistant Examiner* — Amy Shafqat
(74) *Attorney, Agent, or Firm* — Kory D. Christensen

(57) ABSTRACT

The embodiments of the present disclosure disclose an ultrasound imaging method and system, the method may include transmitting a plurality of plane wave ultrasound beams to a scan target and acquiring corresponding plane wave echo signals; transmitting focused ultrasound beams to the scan target and acquiring corresponding focused beam echo signals; acquiring a plurality of velocity components of a target point in the scan target using the plane wave echo signals, and acquiring velocity vectors of the target point according to the plurality of velocity components; acquiring an ultrasound image of the scan target using the focused beam echo signals; and displaying the velocity vector and the ultrasound image.

17 Claims, 6 Drawing Sheets

Related U.S. Application Data continuation of application No. PCT/CN2014/078645, filed on May 28, 2014.

(51) Int. Cl.
   *G01S 7/52* (2006.01)
   *G01S 15/89* (2006.01)
   *A61B 8/14* (2006.01)

(52) U.S. Cl.
   CPC ............ *A61B 8/461* (2013.01); *A61B 8/5223* (2013.01); *G01S 7/52071* (2013.01); *G01S 7/52085* (2013.01); *G01S 15/8984* (2013.01)

(58) Field of Classification Search
   CPC ............ G01S 7/52071; G01S 15/8984; G01S 7/52085
   See application file for complete search history.

(56) References Cited

U.S. PATENT DOCUMENTS

| | | | |
|---|---|---|---|
| 5,355,887 A | 10/1994 | Iizuka | |
| 5,549,111 A | 8/1996 | Wright | |
| 5,581,517 A | 12/1996 | Gee | |
| 5,810,731 A | 9/1998 | Sarvazyan | |
| 5,902,241 A | 5/1999 | Seyed-Bolorforosh | |
| 6,077,226 A | 6/2000 | Washburn | |
| 7,542,790 B2 | 6/2009 | Jensen | |
| 9,060,669 B1 | 6/2015 | Mo | |
| 9,170,330 B2 | 10/2015 | Haugaard | |
| 9,384,530 B2 | 7/2016 | Daigle | |
| 9,427,212 B2 | 8/2016 | Kurita | |
| 9,636,086 B2 | 5/2017 | Jensen | |
| 10,031,226 B2 | 7/2018 | Masuda | |
| 2006/0241429 A1 | 10/2006 | Ustuner | |
| 2006/0241452 A1 | 10/2006 | Cerofolini | |
| 2007/0038086 A1 | 2/2007 | Ohtsuka | |
| 2008/0269611 A1 | 10/2008 | Pedrizzetti | |
| 2009/0187099 A1 | 7/2009 | Burcher | |
| 2009/0326379 A1 | 12/2009 | Daigle | |
| 2011/0066030 A1 | 3/2011 | Yao | |
| 2011/0172538 A1 | 7/2011 | Sumi | |
| 2012/0029350 A1 | 2/2012 | Li | |
| 2012/0089019 A1 | 4/2012 | Fan | |
| 2013/0131511 A1 | 5/2013 | Peterson et al. | |
| 2013/0218014 A1 | 8/2013 | Shim | |
| 2013/0237828 A1 | 9/2013 | Lee et al. | |
| 2013/0279294 A1 | 10/2013 | Angelsen | |
| 2014/0024943 A1 | 1/2014 | Nicolas | |
| 2014/0050048 A1 | 2/2014 | Jensen | |
| 2014/0155738 A1 | 6/2014 | Cheny | |
| 2014/0221816 A1 | 8/2014 | Franke | |
| 2014/0371594 A1 | 12/2014 | Flynn | |
| 2014/0378834 A1 | 12/2014 | Napolitano | |
| 2015/0157280 A1 | 6/2015 | Itai | |
| 2015/0201904 A1 | 7/2015 | Guracar | |
| 2018/0146952 A1 | 5/2018 | Du | |

ULTRASOUND IMAGING METHOD AND SYSTEM

CROSS-REFERENCE TO RELATED APPLICATIONS

This application is a continuation of U.S. patent application Ser. No. 15/362,553, filed Nov. 28, 2016, for ULTRASOUND IMAGING METHOD AND SYSTEM, and PCT/CN2014/078645, filed May 28, 2014, which are incorporated herein by reference.

TECHNICAL FIELD

The present disclosure relates to medical ultrasound imaging and more particularly an ultrasound imaging method and system capable of acquiring velocity vectors of a target.

BACKGROUND

In medical ultrasound imaging, it is very beneficial to detect and acquire a velocity vector of a moving target (such as a moving tissue, blood or another fluid, etc.) in an organism by means of ultrasound imaging.

However, conventional Doppler ultrasound imaging technique can only measure a flow speed in the transmission direction of an ultrasound wave (or, in other words, the propagation direction of an ultrasound wave). In addition, in the conventional method of measuring the velocity of a moving target using focused waves, since the frame rate is limited, in particular when measuring a moving target with much higher velocity, it is difficult to ensure the real-time and high accuracy of the measurement of the velocity, and an aliasing is prone to occur.

SUMMARY

In one aspect, a method of ultrasound imaging may include transmitting a plurality of plane wave ultrasound beams to a scan target; respectively receiving echoes of the plurality of plane wave ultrasound beams to acquire a plurality of sets of plane wave echo signals; transmitting a plurality of focused ultrasound beams to the scan target; respectively receiving echoes of the plurality of focused ultrasound beams to acquire a plurality of sets of focused beam echo signals; acquiring a velocity vector of a target point in the scan target using the plurality of sets of plane wave echo signals; acquiring an ultrasound image of at least part of the scan target using the plurality of sets of focused beam echo signals; and displaying the velocity vector and the ultrasound image.

In an embodiment of the present disclosure, at least a portion of the plurality of plane wave ultrasound beams and at least a portion of the plurality of focused ultrasound beams may be transmitted alternately.

In an embodiment of the present disclosure, the step of acquiring a velocity vector of a target point in the scan target using the plane wave echo signals may include: acquiring at least a first frame of plane wave echo image data and a second frame of plane wave echo image data using the plane wave echo signals; selecting a tracking area in the first frame of plane wave echo image data, the tracking area containing the target point; searching for a tracking result area having the maximum similarity to the tracking area in the second frame of plane wave echo image data; and acquiring the velocity vector of the target point based on the position of the tracking area and of the tracking result area and a time interval between the first frame of plane wave echo image data and second frame of plane wave echo image data.

In an embodiment of the present disclosure, the step of acquiring a velocity vector of a target point in the scan target using the plane wave echo signals may include: acquiring at least two frames of plane wave echo image data using the plane wave echo signals; acquiring a first gradient at the target point along a temporal direction using the plane wave echo image data; acquiring a second gradient at the target point along a propagation direction of the plane wave ultrasound beam using the plane wave echo image data; acquiring a third gradient at the target point along a direction perpendicular to the propagation direction of the plane wave ultrasound beam using the plane wave echo image data; acquiring a fifth velocity component of the target point in the propagation direction of the plane wave ultrasound beam using the plane wave echo signals; calculating a sixth velocity component of the target point in the direction perpendicular to the propagation direction of the plane wave ultrasound beam using the first gradient, the second gradient, the third gradient and the fifth velocity component; and acquiring the velocity vector of the target point by combining the fifth velocity component and the sixth velocity component.

In an embodiment of the present disclosure, the step of acquiring a velocity vector of a target point in the scan target using the plane wave echo signals may include: acquiring at least two frames of plane wave echo image data using the plane wave echo signals; acquiring a first gradient at the target point along a temporal direction using the plane wave echo image data; acquiring a second gradient at the target point along a propagation direction of the plane beam using the plane wave echo image data; acquiring a third gradient at the target point along a direction perpendicular to the propagation direction of the plane beam using the plane wave echo image data; calculating a fifth velocity component of the target point in the propagation direction of the plane wave ultrasound beam and a sixth velocity component in the direction perpendicular to the propagation direction of the plane wave ultrasound beam using the first gradient, the second gradient and the third gradient; and acquiring the velocity vector of the target point by combining the fifth velocity component and the sixth velocity component.

In another aspect, a method of ultrasound imaging may include transmitting a first plane wave ultrasound beam to a scan target, the first plane wave ultrasound beam having a first steered angle; receiving an echo of the first plane wave ultrasound beam to acquire a first plane wave echo signal; transmitting a second plane wave ultrasound beam to the scan target, the second plane wave ultrasound beam having a second steered angle; receiving an echo of the second plane wave ultrasound beam to acquire a second plane wave echo signal; transmitting a focused ultrasound beam to the scan target; receiving an echo of the focused ultrasound beam to acquire a focused beam echo signal; acquiring a first velocity component of a target point in the scan target using the first plane wave echo signal; acquiring a second velocity component of the target point using the second plane wave echo signal; acquiring an ultrasound image of at least part of the scan target using the focused beam echo signal; acquiring a velocity vector of the target point using at least the first velocity component and the second velocity component; and displaying the velocity vector and the ultrasound image.

An embodiment of the present disclosure may further include: transmitting a third plane wave ultrasound beam to the scan target, the third plane wave ultrasound beam having a third steered angle; receiving a third plane wave echo signal of the third plane wave ultrasound beam; and acquiring a third velocity component of the target point using the third plane wave echo signal; where the step of acquiring a velocity vector of the target point using at least the first velocity component and the second velocity component may include acquiring the velocity vector of the target point using at least the first velocity component, the second velocity component and the third velocity component.

In an embodiment of the present disclosure, the step of displaying the velocity vector and the ultrasound image may include displaying the velocity vector on the ultrasound image in a superimposed manner.

In yet another aspect, a method of ultrasound imaging may include transmitting a plurality of first plane wave ultrasound beams to a scan target, each of the first plane wave ultrasound beams having a first steered angle; receiving echoes of the plurality of first plane wave ultrasound beams to acquire a plurality of sets of first plane wave echo signals; transmitting a plurality of second plane wave ultrasound beams to a scan target, each of the second plane wave ultrasound beams having a second steered angle; receiving echoes of the plurality of second plane wave ultrasound beams to acquire a plurality of sets of second plane wave echo signals; transmitting a plurality of focused ultrasound beams to the scan target; receiving echoes of the plurality of focused ultrasound beams to acquire a plurality of sets of focused beam echo signals; acquiring a first velocity component of a target point in the scan target using the plurality of sets of first plane wave echo signals; acquiring a second velocity component of the target point using the plurality of sets of second plane wave echo signals; acquiring an ultrasound image of at least part of the scan target using the plurality of sets of focused beam echo signals; acquiring a velocity vector of the target point using at least the first velocity component and the second velocity component; and displaying the velocity vector and the ultrasound image.

An embodiment of the present disclosure may further include: transmitting a plurality of third plane wave ultrasound beams to the scan target, each of the third plane wave ultrasound beams having a third steered angle; receiving echoes of the plurality of third plane wave ultrasound beams to acquire a plurality of sets of third plane wave echo signals; and acquiring a third velocity component of the target point using the plurality of sets of third plane wave echo signals; where the step of acquiring a velocity vector of the target point using at least the first velocity component and the second velocity component may include: acquiring the velocity vector of the target point using at least the first velocity component, the second velocity component and the third velocity component.

In an embodiment of the present disclosure, at least one portion of the plurality of first plane wave ultrasound beams and at least one portion of the plurality of second plane wave ultrasound beams may be transmitted alternately.

In an embodiment of the present disclosure, at least one of the plurality of focused ultrasound beams may be transmitted between a first plane wave ultrasound beam and a second plane wave ultrasound beam adjacent to each other.

In an embodiment of the present disclosure, at least a portion of the plurality of first plane wave ultrasound beams, at least a portion of the plurality of second plane wave ultrasound beams and at least a portion of the plurality of third plane wave ultrasound beams may be transmitted alternately.

In an embodiment of the present disclosure, at least one of the plurality of focused ultrasound beams may be transmitted between a first plane wave ultrasound beam and a second plane wave ultrasound beam adjacent to each other, or between a first plane wave ultrasound beam and a third plane wave ultrasound beam adjacent to each other, or between a second plane wave ultrasound beam and a third plane wave ultrasound beam adjacent to each other.

In still another aspect, an ultrasound imaging system may include a probe, a transmitting circuit, a receiving circuit and a beam forming unit, a date processor and a display device. The transmitting circuit may excite the probe to transmit a plurality of plane wave ultrasound beams to a scan target, and excite the probe to transmit a plurality of focused ultrasound beams to the scan target; the receiving circuit and the beam forming unit may respectively receive echoes of the plurality of plane wave ultrasound beams so as to acquire a plurality of sets of plane wave echo signals and receive echoes of the plurality of focused ultrasound beams so as to acquire a plurality of sets of focused beam echo signals; the date processor may acquire a velocity vector of a target point in the scan target using the plurality of sets of plane wave echo signals, and acquire an ultrasound image of at least part of the scan target using the plurality of sets of focused beam echo signals; and the display device may display the velocity vector and the ultrasound image.

In an embodiment of the present disclosure, at least one portion of the plurality of plane wave ultrasound beams and at least one portion of the plurality of focused ultrasound beams may be transmitted alternately.

In yet another aspect, an ultrasound imaging system may include a probe, a transmitting circuit, a receiving circuit and a beamformer, a date processor and a display device. The transmitting circuit may excite the probe to transmit first plane wave ultrasound beams at a first steered angle, transmit second plane wave ultrasound beams at a second steered angle and transmit focused ultrasound beams to a scan target; the receiving circuit and the beamformer may receive echoes of the first plane wave ultrasound beams so as to acquire first plane wave echo signals, receive echoes of the second plane wave ultrasound beams so as to acquire second plane wave echo signals and receive echoes of the focused ultrasound beams so as to acquire focused beam echo signals; the date processor may acquire a first velocity component of a target point in the scan target using the first plane wave echo signals, acquire a second velocity component of the target point using the second plane wave echo signals and acquiring a velocity vector of the target point using at least the first velocity component and the second velocity component, and the date processor also may acquire an ultrasound image of at least part of the scan target using the focused beam echo signals; and the display device may display the velocity vector and the ultrasound image.

In an embodiment of the present disclosure, the transmitting circuit may also excite the probe to transmit third plane wave ultrasound beams to the scan target at a third steered angle; the receiving circuit and the beamformer may also receive echoes of the third plane wave ultrasound beams so as to acquire third plane wave echo signals; and the date processor may also acquire a third velocity component of the target point using the third plane wave echo signals, and acquire the velocity vector of the target point using at least the first velocity component, the second velocity component and the third velocity component.

In an embodiment of the present disclosure, the display device may display the velocity vector on the ultrasound image in a superimposed manner.

Further in another aspect, an ultrasound imaging system may include a probe, a transmitting circuit, a receiving circuit and a beamformer, a date processor and a display device. The transmitting circuit may excite the probe to transmit a plurality of first plane wave ultrasound beams at a first steered angle, transmit a plurality of second plane wave ultrasound beams at a second steered angle and transmit a plurality of focused ultrasound beams to a scan target; the receiving circuit and the beamformer may receive echoes of the plurality of first plane wave ultrasound beams so as to acquire a plurality of sets of first plane wave echo signals, receive echoes of the plurality of second plane wave ultrasound beams so as to acquire a plurality of sets of second plane wave echo signals and receive echoes of the plurality of focused ultrasound beams so as to acquire a plurality of sets of focused beam echo signals; the date processor may acquire a first velocity component of a target point in the scan target using the plurality of sets of first plane wave echo signals, acquire a second velocity component of the target point using the plurality of sets of second plane wave echo signals and acquire a velocity vector of the target point at least using the first velocity component and the second velocity component; and the date processor may also acquire an ultrasound image of at least part of the scan target using the plurality of sets of focused beam echo signals; and the display may display the velocity vector and the ultrasound image.

In an embodiment of the present disclosure, the transmitting circuit may also excite the probe to transmit a plurality of third plane wave ultrasound beams to the scan target at a third steered angle; the receiving circuit and the beamformer may also receive echoes of the plurality of third plane wave ultrasound beams so as to acquire a plurality of sets of third plane wave echo signals; and the date processor may also acquire a third velocity component of the target point using the plurality of sets of third plane wave echo signals, and acquire the velocity vector of the target point at least using the first velocity component, the second velocity component and the third velocity component.

In an embodiment of the present disclosure, the display device may display the velocity vector on the ultrasound image in a superimposed manner.

In an embodiment of the present disclosure, at least one portion of the plurality of first plane wave ultrasound beams and at least one portion of the plurality of second plane wave ultrasound beams may be transmitted alternately.

In an embodiment of the present disclosure, at least one of the plurality of focused ultrasound beams may be transmitted between a first plane wave ultrasound beam and a second plane wave ultrasound beam adjacent to each other.

In an embodiment of the present disclosure, at least one portion of the plurality of first plane wave ultrasound beams, at least one portion of the plurality of second plane wave ultrasound beams and at least one portion of the plurality of third plane wave ultrasound beams may be transmitted alternately.

In an embodiment of the present disclosure, at least one of the plurality of focused ultrasound beams may be transmitted between the first plane wave ultrasound beam and the second plane wave ultrasound beam adjacent to each other, or between the first plane wave ultrasound beam and the third plane wave ultrasound beam adjacent to each other, or between the second plane wave ultrasound beam and the third plane wave ultrasound beam adjacent to each other.

Various other features, objects, and advantages of the invention will be made apparent to those skilled in the art from the accompanying drawings and detailed description thereof.

DETAILED DESCRIPTION

In the following detailed description, reference is made to the accompanying drawings that form a part hereof, and in which is shown by way of illustration specific embodiments that may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken as limiting the scope of the invention.

Figure 1:
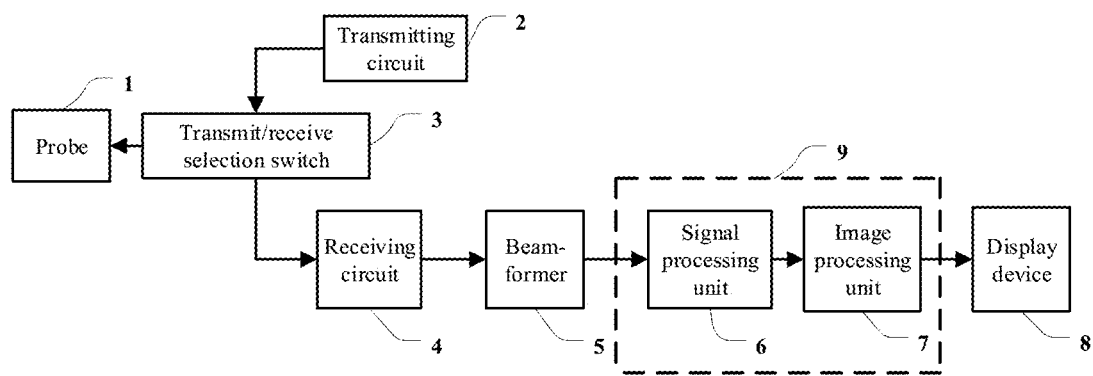
FIG. 1 is a schematic block diagram of an ultrasound imaging system according to an embodiment of the present disclosure.

FIG. 1 is a schematic structural diagram of an ultrasound imaging system according to an embodiment of the present disclosure. As shown in FIG. 1, the ultrasound imaging system may generally include: a probe 1, a transmitting circuit 2, a transmit/receive selection switch 3, a receiving circuit 4, a beamformer 5, a signal processing unit 6, an image processing unit 7 and a display device 8. The signal processing unit 6 and image processing unit 7 may be collectively referred to herein as a data processing device 9. All of the units and devices herein may be implemented using any suitable combination of hardware, software, and/or firmware, and may include various microprocessors, computer-readable media, and the like, as known to one of ordinary skill in the art.

In the process of ultrasound imaging, the transmitting circuit 2 may send a delay-focused transmission pulse with a certain amplitude and polarity to the probe 1 via the transmit/receive selection switch 3. The probe 1 may be excited by the transmission pulse to transmit an ultrasound wave to the scan target (such as an organ, tissue or a blood vessel in a human body or the body of an animal, etc., not shown in the figure), receive ultrasound echo carrying information about the scan target reflected back from a target area after a certain delay, and convert the ultrasound echo into electrical signals. The receiving circuit 4 may receive the electrical signals generated by the conversion of the probe 1 to acquire ultrasound echo signals, and send these ultrasound echo signals to the beamformer 5. The beamformer 5 may perform the following processing on the ultrasound echo signals, such as focus delay processing, weighted processing and channel summation processing, etc., and then send the ultrasound echo signals to the signal processing unit 6 for relevant signal processing.

The ultrasound echo signals processed by the signal processing unit 6 may be sent to the image processing unit 7. According to different imaging modes required by a user, the image processing unit 7 may perform different types of processing on the signals to acquire image data of different modes, and then form ultrasound image of different modes, such as a B mode image, C mode image or D mode image, by performing processing such as logarithmic compression, dynamic range adjustment, digital scan conversion, and the like.

The ultrasound image generated by the image processing unit 7 may be sent to the display device 8 to be displayed.

The probe 1 may generally include a transducer array with a plurality of transducers. Each time an ultrasound wave may be transmitted, all or one portion of the transducers of the probe 1 may participate in the ultrasound wave transmission. In this case, each of the transducers participating in the ultrasound wave transmission may be respectively excited by the transmission pulse and respectively transmit an ultrasound wave. The ultrasound waves respectively transmitted by these transducers may be synthesised during the propagation to form an ultrasound beam transmitted to the scan target.

The transducers participating in the ultrasound wave transmission can be excited simultaneously by the transmission pulse, or there can be a certain delay between the times when the transducers participating in the ultrasound wave transmission are excited by the transmission pulse. The ultrasound beams transmitted by the transducers can be superposed at a pre-set location by controlling the delay between the times when the transducers participating in the ultrasound wave transmission can be excited by the transmission pulse, such that the ultrasound wave may be strongest at the pre-set location, that is to say, the ultrasound waves transmitted by the transducers can be "focused" at the pre-set location, the focusing pre-set location can be referred to as a "focal point", and in this way, the acquired synthesised ultrasound beams may be focused beams at the focal point, which are referred to herein as "focused ultrasound beams".

Alternatively, the ultrasound waves transmitted by the transducers participating in the ultrasound wave transmission may also not be focused in the propagation process by controlling the delay between the times when the transducers participating in the ultrasound wave transmission can be excited by the transmission pulse, and also may not be completely diffused, thus roughly forming a plane wave overall on a plane. This unfocused plane wave is referred to herein as a "plane wave ultrasound beam".

When transmitting the plane wave ultrasound beam, by controlling the delay between the time when the transducers participating in the ultrasound wave transmission are excited by the transmission pulse, the propagation direction of the plane wave ultrasound beam can be made to form a pre-set angle relative to a surface of an ultrasound wave transmitted by the probe 1, and this angle is referred to herein as a "steered angle" of the plane wave ultrasound beam.

Figure 2:
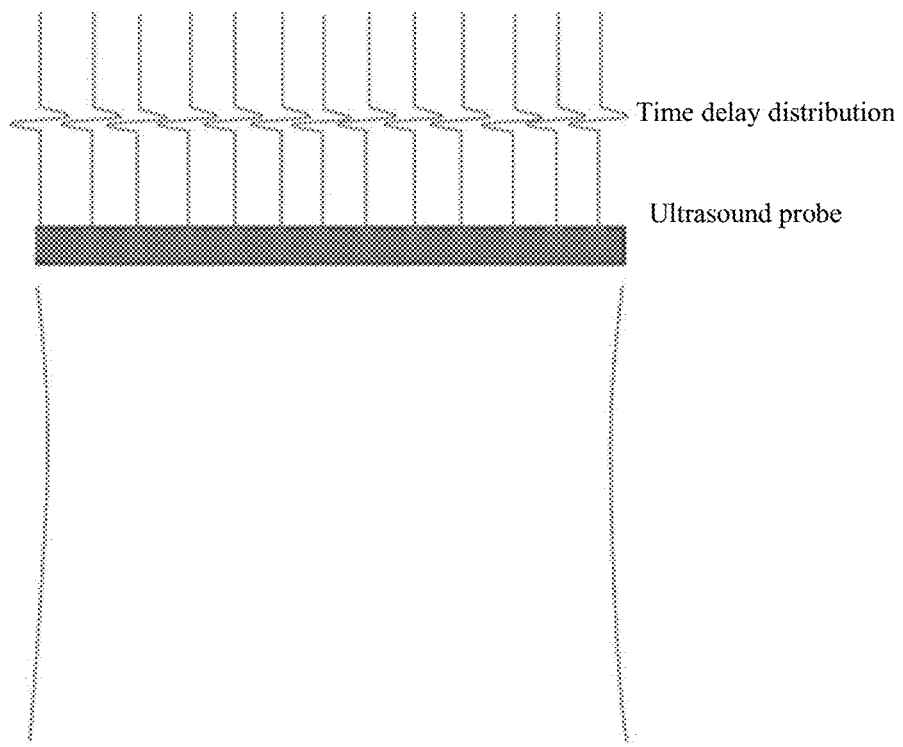
FIG. 2 is a schematic diagram of non-steered plane wave transmission according to an embodiment of the present disclosure.

For example, FIG. 2 shows a non-steered plane wave, at which point there may be no delay between the transducers participating in the ultrasound wave transmission (i.e. there may be no delay between the time when the transducers are excited by the transmission pulse), and the transducers may be simultaneously excited by the transmission pulse. The ultrasound beam generated may be a plane wave, i.e. a plane wave ultrasound beam, and the propagation direction of the plane wave ultrasound beam may be roughly perpendicular to a surface of the ultrasound wave transmitted by the probe 1, i.e. the steered angle of the plane wave ultrasound beam may be 90°.

Figure 3:
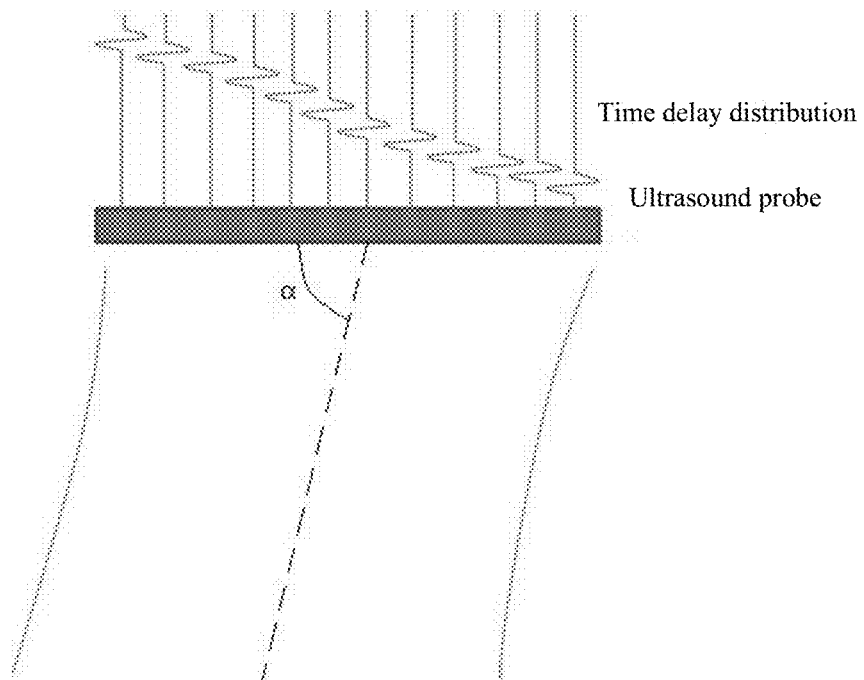
FIG. 3 is a schematic diagram of steered plane wave transmission according to an embodiment of the present disclosure.

FIG. 3 shows a steered transmitted plane wave, at which point there may be a pre-set delay between the transducers participating in the ultrasound wave transmission (i.e. there may be a predetermined delay between the time when the transducers are excited by the transmission pulse), and the transducers may be excited by the transmission pulse in a pre-set order. The ultrasound beam generated may be a plane wave, i.e. a plane wave ultrasound beam, and the propagation direction of the plane wave ultrasound beam may be at a certain angle with respect to the surface of the ultrasound wave transmitted by the probe 1 (for example, the angle α in FIG. 3), i.e. this angle can be the steered angle of the plane wave ultrasound beam.

It can be easily understood that in the embodiments of the present disclosure, the aforesaid "steered angle" can also be defined in another manner, as long as it is possible to express the steered of the propagation direction of the plane wave ultrasound beam relative to the surface of the ultrasound wave transmitted by the ultrasound probe.

Figure 4:
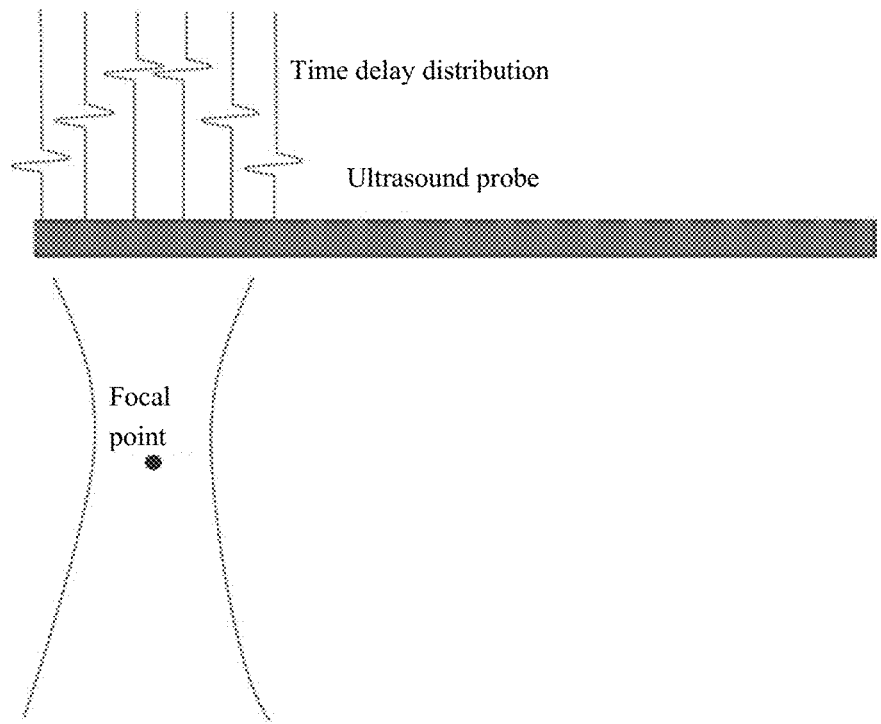
FIG. 4 is a schematic diagram of focused ultrasound beams according to an embodiment of the present disclosure.

FIG. 4 is a schematic diagram of the transmission of focused ultrasound beams. Herein, the transducers participating in the ultrasound wave transmission (in FIG. 4, only some transducers in the probe 1 may participate in the ultrasound wave transmission) may operate by way of a pre-set transmission delay (i.e. there may be a pre-set delay between the times when the transducers participating in the ultrasound wave transmission can be excited by the transmission pulse), and the ultrasound wave transmitted by the transducers may be focused at the focal point, for forming focused ultrasound beams.

The plane wave ultrasound beam generally practically may cover the entire imaging area of the probe 1, and therefore, when using the plane wave ultrasound beam for imaging, one frame of ultrasound image can be obtained through one plane wave transmission, and thus the imaging frame rate can be very high. Under normal circumstances, the frame rate using plane wave ultrasound beam imaging can be several dozen or even several hundred times higher than the frame rate using focused ultrasound beams imaging. However, the energy of the plane wave ultrasound beam may be relatively dispersed, and therefore, the signal-to-noise ratio of the echo signal acquired may be relatively low, the quality of the ultrasonic image may be lower, and the plane wave ultrasound beam may be unfocused, and therefore, the resolution of the plane wave ultrasound beam imaging may be a lower than the focused ultrasound beam imaging.

In addition, when using focused ultrasound beam imaging, because the beam can be focused at the focal point, thereby only one or several scan lines can be obtained each time, multiple focused ultrasound beam transmissions can be required to be able to obtain all the scan lines in the imaging area, whereby all the scan lines may be combined to obtain a frame of an ultrasound image of the imaging area. Therefore, the frame rate may be relatively low when using focused ultrasound beam imaging. However, energy is concentrated when the focused ultrasound beam may be transmitted each time, and imaging can be only performed at the site of the energy concentration; therefore, the signal-to-noise ratio of the echo signal acquired may be high, the quality of ultrasound image acquired may be good, the main lobe of the focused ultrasound beam may be narrow, and the side lobe of the focused ultrasound beam may be lower, so the lateral resolution of the ultrasound image acquired may be also higher.

The embodiments of the present disclosure may provide an ultrasound imaging method capable of acquiring the velocity vector (described below in detail) of a point in a flow field of a fluid (such as blood or another fluid in an organism) in a scan target (such as a blood vessel or another vessel within which a fluid is flowing in an organism), and both the plane wave ultrasound beams and the focused ultrasound beams may be used in the process of imaging. The plane wave ultrasound beam may be used to acquire the velocity vector, whereby the advantages of high frame rate of plane wave ultrasound beam imaging may be fully used to meet the requirements for a high frame rate when measuring a fluid velocity using ultrasound imaging; while the focused ultrasound beam may be used to acquire the ultrasound image of the scan target (for example, acquiring an ultrasound image of a blood vessel wall or tissue around a blood vessel or another vessel and a tissue around the vessel in an organism, etc.), whereby the advantages of a high signal-to-noise ratio of the echo signal, a high resolution of the image, and a high lateral resolution of the focused ultrasound beam imaging may be fully used in order to acquire a good image for observation by the user. Hereinafter, a detailed explanation is given in conjunction with specific embodiments.

Figure 5:
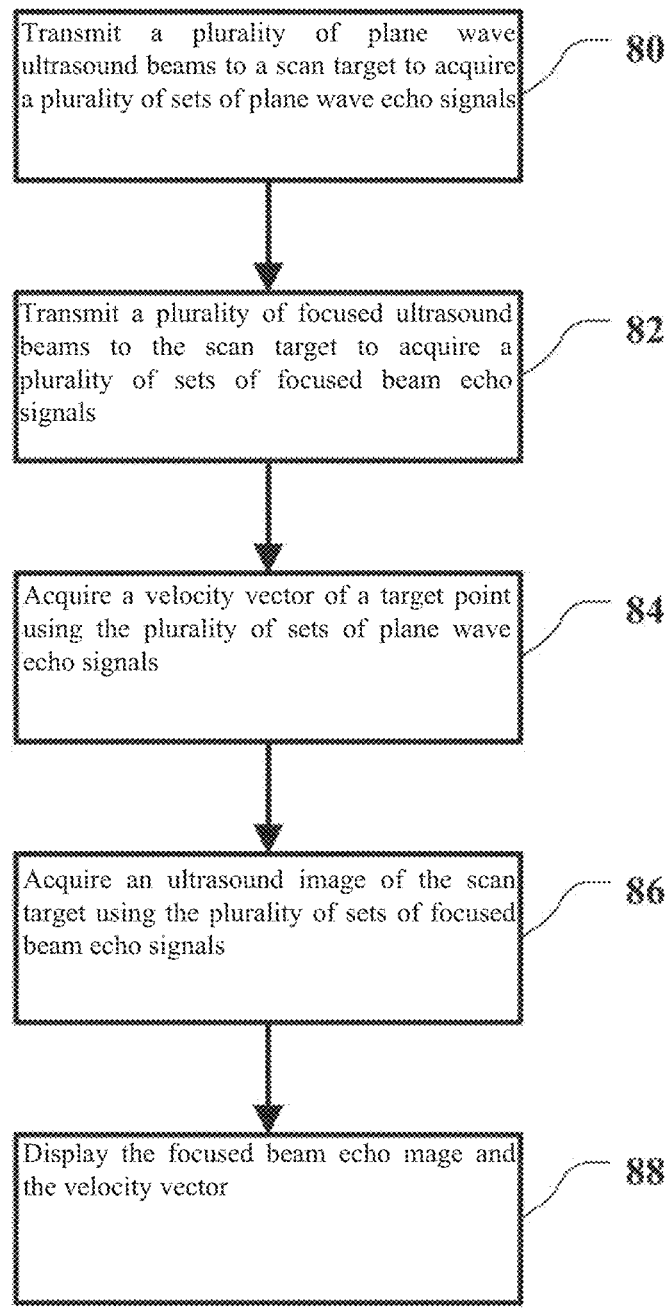
FIG. 5 is a schematic flow diagram of an ultrasound imaging method according to an embodiment of the present disclosure.

FIG. 5 is a schematic flow diagram of an ultrasound imaging method according to an embodiment of the present disclosure. It should be understood that although each step in the flow diagram in FIG. 5 may be displayed in succession as indicated by an arrow, these steps may be not necessarily executed in succession in the order indicated by the arrows. Unless expressly described herein, the execution of these steps may be not limited to a strict order, instead, the steps can be executed in another order. In addition, at least some steps in FIG. 5 may include multiple sub-steps or multiple stages. These sub-steps or stages may be not necessarily executed or completed at the same moment, but can be executed at different times, and the order of execution thereof may be also not necessarily in succession, but can be executed in turn or alternately with at least some other steps or sub-steps or stages of other steps.

As shown in FIG. 5, in an embodiment of the present disclosure, an ultrasound imaging method may include the steps as follows.

In step 80, the transmitting circuit 2 may excite the probe 1 to transmit a plurality of plane wave ultrasound beams to a scan target (such as a blood vessel or another vessel within which a fluid is flowing in an organism, etc.). These plane wave ultrasound beams can be unfocused plane waves as stated previously. In an embodiment of the present disclosure, these plane wave ultrasound beams may have the same steered angle.

Each transmitted plane wave ultrasound beam may enter the scan target, and a fluid and a tissue in the scan target may disperse and/or reflect this plane wave ultrasound beam. The probe 1 may receive echoes (referred to in the present disclosure as plane wave ultrasound beam echoes) formed by the dispersion and/or reflection of the plane wave ultrasound beam by the scan target, and convert these echoes into electrical signals. The electrical signals may be processed by multiple units such as the receiving circuit 4 and the beam-former 5, etc., to obtain echo signals corresponding to the transmitted plane wave ultrasound beam, which is referred to herein as plane wave echo signals. Each transmitted plane wave ultrasound beam may be used to correspondingly obtain a set of plane beam echo signals, and therefore, a plurality of sets of plane wave echo signals may be obtained by transmitting a plurality of plane wave ultrasound beams.

In step 82, the transmitting circuit 2 may excite the probe 1 to transmit a plurality of focused ultrasound beams to the scan target. Each transmitted focused ultrasound beam may enter the scan target, and may be focused at a pre-set location (i.e. a focal point) in the scan target. A fluid and a tissue in the scan target may disperse and/or reflect this focused ultrasound beam. The probe 1 may receive echoes (referred to in the present disclosure as focused ultrasound beam echoes) formed by the dispersion and/or reflection of the focused ultrasound beam by the scan target, and convert these echoes into electrical signals. The electrical signals may be processed by multiple units such as the receiving circuit 4 and the beamformer 5, etc., to obtain echo signals corresponding to the transmitted focused ultrasound beams, which are referred to herein as focused beam echo signals.

In this embodiment of the present disclosure, a plurality of focused ultrasound beams may be transmitted, image data of one or several scan lines of the scan target can be acquired each time, and at least one portion of these focused ultrasound beams transmitted multiple times can be focused at different focal points; therefore image data of one or several scan lines at different locations in the scan target can be acquired in this way. Then, the image data of the one or several scan lines acquired in multiple transmissions may be combined to obtain one entire image or at least part of one entire image of the scan target.

In an embodiment of the present disclosure, at least one portion of the aforesaid plurality of plane wave ultrasound beams and at least one portion of the aforesaid plurality of focused ultrasound beams may be alternately transmitted, i.e. at least one portion of the plurality of focused ultrasound beams may be transmitted at a time between the transmission times of two plane ultrasonic beams adjacent at the front and the back.

After acquiring plane wave echo signals, in step 84, the velocity vector of a target point (for example, a point or a location of interest in the scan target) in the scan target can be acquired using the acquired plurality of sets of plane wave echo signals.

In the embodiment of the present disclosure, multiple methods can be used to acquire the velocity vector of the target point using the acquired plurality of sets of plane wave echo signals.

For example, in one embodiment of the present disclosure, a method of similar speckle tracking can be used to acquire the velocity vector of the target point using the acquired plurality of sets of plane wave echo signals.

In this embodiment, the step of acquiring the velocity vector of the target point may include the steps as follows.

Firstly, at least two frames of plane wave echo image data can be acquired using the aforesaid plurality of sets of plane wave echo signals, for example, at least a first frame of plane wave echo image data and a second frame of plane wave echo image data can be acquired. As stated previously, the plane wave ultrasound beams may be roughly propagated across the entire imaging area, and therefore, generally, one set of plane wave echo signals can be acquired corresponding to one transmission of a plane wave ultrasound beam (i.e. one plane wave ultrasound beam), one frame of plane wave echo image data can be acquired by processing one set of plane wave echo signals. The ultrasound image date of the scan target may be acquired by processing on the plane wave echo signal correspondingly acquired by the plane wave ultrasound beam, which is referred herein to as "plane wave echo image data".

Then, a tracking area may be selected in the first frame of plane wave echo image data, and the tracking area can contain the target point for which the velocity vector can be to be acquired. For example, the tracking area can select a certain neighbourhood of the target point or a certain data block containing the target point.

Next, a search may be performed for an area corresponding to the tracking area in the second frame of plane wave echo image data, for example, searching for an area having the maximum similarity to the aforesaid tracking area as a tracking result area. Here, a measurement method commonly used in the art can be used to measure the similarity.

Then, the velocity vector of the target point can be acquired according to the position of the aforesaid tracking area and of the aforesaid tracking result area and a time interval between the first frame of plane wave echo image data and second frame of plane wave echo image data. For example, the size of the velocity vector can be acquired by means of the distance between the tracking area and the tracking result area divided by the time interval between the first frame of plane wave echo image data and second frame of plane wave echo image data, and the direction of the velocity vector can be the direction of a connecting line from the tracking area to the tracking result area.

In another embodiment, acquiring the velocity vector of the target point can be based on the temporal gradient and the spatial gradient at the target point.

The principle of this method is as follows.

Given that the plane wave echo image data correspondingly acquired through the plane wave ultrasound beam may be P(x(t), z(t)), where P is derived in the temporal direction, the following can be obtained based on a chain rule:

$$\frac{dP(x(t)z(t))}{dt} = \frac{\partial P}{\partial x}\frac{dx}{dt} + \frac{\partial P}{\partial z}\frac{dz}{dt}, \tag{1}$$

where when taking the z direction as the propagation direction of the plane wave ultrasound beam, and the x direction as the direction perpendicular to the propagation direction of the plane wave ultrasound beam, then $$\frac{dz}{dt}$$

may be a velocity component $v_z$ along the z direction (i.e. the propagation direction of the plane wave ultrasound beam), i.e.

$$v_z = \frac{dz}{dt}; \text{ and } \frac{dx}{dt}$$

is a velocity component $v_x$ along the x direction (i.e. the direction perpendicular to the propagation direction of the plane wave ultrasound beam), i.e.

$$v_x = \frac{dx}{dt}.$$

Therefore, the aforesaid formula can be written as:

$$\frac{dP(x(t), z(t))}{dt} = \frac{\partial P}{\partial x}v_x + \frac{\partial P}{\partial z}v_z, \tag{2}$$

where $$\frac{\partial P}{\partial x}, \frac{\partial P}{\partial z}$$

can be acquired by seeking the gradient of the plane wave echo signal image data along the x and z directions respectively; and $$\frac{dP(x(t), z(t))}{dt}$$

can be acquired by seeking the gradient along the temporal direction of a point on the plane wave echo image data according to at least two frames of plane wave echo image data. In this way, in formula (2), only $v_x$ and $v_z$ may be unknown quantities, and these two unknown quantities may be the two velocity components to be obtained.

Therefore, in the embodiment of the present disclosure, as regards a certain target point in the image, firstly, according to the acquired plane wave echo image data, a gradient in the aforesaid x direction, z direction and temporal direction at this target point can be calculated, and then the velocity components $v_x$ and $v_z$ can be calculated according to formula (2).

In the embodiment of the present disclosure, many suitable methods can be used to acquire the velocity components $v_x$ and $v_z$, and the following are several listed examples.

For example, generally, the velocity of movement of a scan target or a moving part therein can be obtained by Doppler processing on the ultrasound echo signal with the Doppler principle in ultrasound imaging. For example, after obtaining the ultrasound echo signals, the velocity of movement of the scan target or a moving part therein can be obtained using the ultrasound echo signal through an auto-correlation estimation method or a cross-correlation estimation method. Any method that can be used to calculate the velocity of movement of the scan target or a moving part therein by processing an ultrasound echo signal with Doppler processing, may be the means currently used in the art or may be the future means that could be used to calculate the velocity of movement of the scan target or a moving part therein using the ultrasound echo signals, and will not be described again herein.

At this point, the velocity of movement of the scan target or a moving part therein acquired by Doppler processing may be the velocity in the propagation direction of the ultrasound beam. Since the direction of movement of the scan target or a moving part therein may be not necessarily consistent with the propagation direction of the ultrasound beam, therefore the velocity of movement of the scan target or a moving part therein acquired by transmitting (or propagating) the ultrasound beam in one direction may be actually a velocity component of the actual velocity of movement of the scan target or a moving part therein in the propagation direction of the ultrasound beam (the actual velocity of movement may be a vector containing information about the size and direction).

Therefore, in an embodiment of the present disclosure, the aforesaid velocity component $v_z$ in the z direction (i.e. the propagation direction of the plane wave ultrasound beam) can be obtained by Doppler processing on the acquired plane wave echo signal. After acquiring $v_z$, $v_x$ can easily be calculated according to formula (2).

Therefore, in an embodiment of the present disclosure, the step of acquiring the velocity vector of the target point in the scan target using plane wave echo signals may include:

acquiring at least two frames of plane wave echo image data using the acquired plane wave echo signals;

acquiring a first gradient at the target point along a temporal direction (i.e., the aforesaid gradient along the temporal direction) using the plane wave echo image data;

acquiring a second gradient at the target point along a propagation direction of the plane wave ultrasound beam (for example, the aforesaid gradient along the z direction) using the plane wave echo image data;

acquiring a third gradient at the target point along a direction perpendicular to the propagation direction of the plane wave ultrasound beam (for example, the aforesaid gradient along the x direction) using the plane wave echo image data;

acquiring a fifth velocity component (for example, the aforesaid $v_z$) of the target point in the propagation direction of the plane beam using the aforesaid plane wave echo signals;

calculating a sixth velocity component (for example, the aforesaid $v_x$) of the target point in the direction perpendicular to the propagation direction of the plane wave ultrasound beam using the aforesaid first gradient, second gradient, third gradient and fifth velocity component; and acquiring the velocity vector of the target point by combining the fifth velocity component and the sixth velocity component.

In this way, the velocity vector of the target point can be acquired.

Moreover, in another embodiment of the present disclosure, in view of the fact that formula (2) may be an equation involving two unknown quantities, multiple equations can be reached based on multiple sets of measurements and calculation results, and in this way, the least square method can be used to solve and calculate these two unknown quantities, and then the velocity vector of the target point can be acquired by combining the two unknown quantities. The principle of the method in this embodiment may be summarised below.

Using the least square method, the aforesaid formula (2) can be written as $$\begin{bmatrix} P_1^t \\ P_2^t \\ \vdots \\ P_N^t \end{bmatrix} = \begin{bmatrix} P_1^x & P_1^z \\ P_2^x & P_2^z \\ \vdots & \vdots \\ P_N^x & P_N^z \end{bmatrix} \begin{bmatrix} v_x \\ v_z \end{bmatrix} + \begin{bmatrix} \varepsilon_1 \\ \varepsilon_2 \\ \vdots \\ \varepsilon_N \end{bmatrix}, \quad (3)$$

where $$P_i^t = \frac{dP_i(x(t), z(t))}{dt}, P_i^x = \frac{\partial P_i}{\partial x}, P_i^z = \frac{\partial P_i}{\partial z},$$

and the subscript i represents the corresponding value in the ith calculation. Given that there is a total of N calculations, and since the time accounted for the Nth calculation may be very short, it is assumed that blood velocity within this period of time remains unchanged. $\varepsilon_i$ represents a random error. Here, formula (3) satisfies the Gauss-Markov theorem, solving:

$$\begin{bmatrix} v_x \\ v_z \end{bmatrix} = (A^T A)^{-1} A^T u, \text{ where} \quad (4)$$

$$A = \begin{bmatrix} P_1^x & P_1^z \\ P_2^x & P_2^z \\ \vdots & \vdots \\ P_N^x & P_N^z \end{bmatrix}, u = \begin{bmatrix} P_1^t \\ P_2^t \\ \vdots \\ P_N^t \end{bmatrix}.$$

According to the Gauss-Markov theorem, the variance in the random error $\varepsilon_i$ can be represented as $$\text{var}(\varepsilon_i) = \sigma_A^2, \quad (5)$$

as stated previously, using the Doppler ultrasound method to measure the velocity $v_z$ in the z direction (the propagation direction of the plane wave ultrasound beam), with reference to formula (3), $$V_D = B \begin{bmatrix} v_x \\ v_z \end{bmatrix} + \varepsilon_j, \quad (6)$$

Where $V_D = \begin{bmatrix} v_1 \\ v_2 \\ \vdots \\ v_N \end{bmatrix}, B = \begin{bmatrix} 0 & 1 \\ 0 & 1 \\ \vdots & \vdots \\ 0 & 1 \end{bmatrix}.$ $V_D$ is a set of velocity values at different times measured by using the Doppler ultrasound method, $v_z$ in formula (6) is an average value acquired by the Doppler ultrasound method, and given this, the variance of $\varepsilon_j$ can be acquired:

$$\text{var}(\varepsilon_j) = \sigma_B^2 \quad (7)$$

the two different variances calculated according to formulae (5) and (7) use a weighted least square method $$\left(w \begin{bmatrix} A \\ B \end{bmatrix}\right)^T \left(w \begin{bmatrix} A \\ B \end{bmatrix}\right) \begin{bmatrix} v_x \\ v_z \end{bmatrix} = \left(w \begin{bmatrix} A \\ B \end{bmatrix}\right)^T \begin{bmatrix} u \\ V_D \end{bmatrix}, \quad (8)$$

where the weighting coefficient $$w = \begin{bmatrix} I_A \sqrt{\frac{1}{\sigma_A^2}} & O \\ O & I_B \sqrt{\frac{1}{\sigma_B^2}} \end{bmatrix}$$

O is a zero matrix, $I_A$ and $I_B$ are unit matrix, and the orders thereof respectively correspond to the row numbers of matrices A and B.

In this way, the two velocity components $v_x$ and $v_z$ can be solved and acquired, and after acquiring the two velocity components, the velocity vector of the target point can be obtained through combining the two velocity components.

Therefore, in an embodiment of the present disclosure, the step of acquiring the velocity vector of the target point in the scan target using plane wave echo signals may include:

acquiring a first gradient at the target point along a temporal direction (i.e. the aforesaid gradient along the temporal direction) using the plane wave echo image data;

acquiring a second gradient at the target point along a propagation direction of the plane wave ultrasound beam (for example, the aforesaid gradient along the z direction) using the plane wave echo image data;

acquiring a third gradient at the target point along a direction perpendicular to the propagation direction of the plane wave ultrasound beam (for example, the aforesaid gradient along the x direction) using the plane wave echo image data;

calculating a fifth velocity component (for example, the aforesaid $v_z$) of the target point in the propagation direction of the plane wave ultrasound beam and a sixth velocity component (for example, the aforesaid $v_x$) of the target point in the direction perpendicular to the propagation direction of the plane wave ultrasound beam using the acquired first gradient, second gradient and third gradient; and acquiring the velocity vector of the target point by combining the fifth velocity component and the sixth velocity component.

In an embodiment of the present disclosure, after acquiring a plurality of sets of focused beam echo signals, in step 86, an ultrasound image of at least part of a scan target can be acquired using the plurality of sets of focused beam echo signals, i.e. performing corresponding processing on the focused beam echo signals so as to acquire the ultrasound image of at least part of a scan target. From the description as stated previously, each focused ultrasound beam may be generally focused at a focal point, and therefore, image data of one or more scan lines of the scan target can be generally acquired using each focused beam echo signal. Here, an image (or image data of the one or more scan lines) of at least part of the scan target acquired using the focused beam echo signal may be a B mode image (or B mode image data), and may also be an ultrasound image (or ultrasound image data) of any other suitable modes. Each set of the plurality of sets of focused beam echo signals may be respectively processed to obtain the image data of the one or more scan lines of the scan target. One entire ultrasound image or at least part of one entire ultrasound image of the scan target can be acquired by combining the image data of these one or more scan lines.

Any suitable methods that are currently used in the art and could be generally used in the future can be used to acquire the ultrasound image (or ultrasound image data) of at least part of the scan target using the acquired focused beam echo signal, and will not be described again herein.

After acquiring the velocity vector of the target point in the scan target and the ultrasound image of at least part of the scan target, in step 88, the velocity vector and the ultrasound image can be displayed. For example, the velocity vector and the ultrasound image can be simultaneously displayed on the display device 8. For example, in the embodiment of the present disclosure, the velocity vector can be displayed on the ultrasound image in a superimposed manner.

In an embodiment of the present disclosure, step 84 and/or step 86 as stated previously can be executed by the date processor 9 of the ultrasound imaging system. In an embodiment of the present disclosure, the date processor 9 may include the signal processing unit 6 and/or the image processing unit 7, and step 84 and/or step 86 as stated previously can be executed by the signal processing unit 6 and/or the image processing unit 7.

In the aforesaid embodiment, plane wave ultrasound beams (i.e. transmitted plane wave ultrasound beams having the same steered angle) in the same direction can be used to acquire the velocity vector of the target point in the scan target by processing plane wave echo signals in the same direction. In another embodiment of the present disclosure, plane wave ultrasound beams (i.e. plane wave ultrasound beams having different steered angles may be emitted to the scan target) in a plurality of different directions can also be used to acquire the velocity vector of the target point in the scan target.

Figure 6:
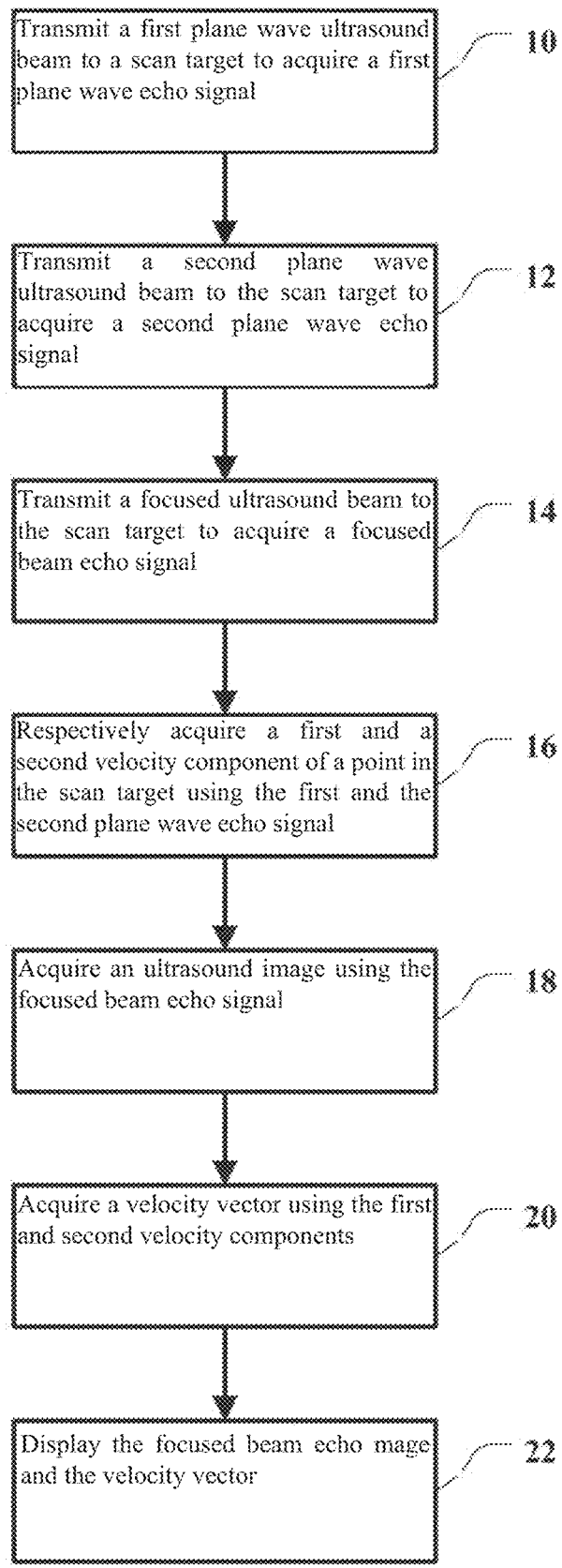
FIG. 6 is a schematic flow diagram of an ultrasound imaging method according to an embodiment of the present disclosure.

For example, FIG. 6 is a schematic flow diagram of an ultrasound imaging method according to an embodiment of the present disclosure. It should be understood that although each step in the flow diagram in FIG. 6 may be displayed in succession as indicated by an arrow, these steps may be not necessarily executed in succession in the order indicated by the arrows. Unless expressly described herein, the execution of these steps may be not limited to a strict order, instead, the steps can be executed in another order. In addition, at least some steps in FIG. 6 may include multiple sub-steps or multiple stages. These sub-steps or stages may be not necessarily executed or completed at the same moment, but can be executed at different times, and the order of execution thereof may be also not necessarily in succession, but can be executed in turn or alternately with at least some other steps or sub-steps or stages of other steps.

As shown in FIG. 6, in an embodiment of the present disclosure, an ultrasound imaging method may include the steps as follows.

In step 10, the transmitting circuit 2 may excite the probe 1 to transmit a first plane wave ultrasound beam to a scan target (such as a blood vessel or another vessel within which a fluid is flowing in an organism, etc.). The first plane wave ultrasound beam can be an unfocused plane wave as stated previously, and may have a first steered angle. The transmitted first plane wave ultrasound beam may enter the scan target, a fluid and a tissue in the scan target disperse and/or reflect this first plane wave ultrasound beam. The probe 1 may receive echoes (referred to herein as first plane wave ultrasound beam echoes) formed by the dispersion and/or reflection of the first plane wave ultrasound beam through the scan target, and convert these echoes into electrical signals. The electrical signals may be processed by multiple units such as the receiving circuit 4 and the beamformer 5, etc., to obtain echo signals corresponding to the transmitted first plane wave ultrasound beams, which are referred to in this present disclosure as first plane wave echo signals.

Similarly, in step 12, the transmitting circuit 2 may excite the probe 1 to transmit a second plane wave ultrasound beam to the scan target. The second plane wave ultrasound beam can be an unfocused plane wave as stated previously, and may have a second steered angle. The second steered angle can be different from the aforesaid first steered angle. That is to say, a propagation direction of the second plane wave ultrasound beam may be actually different from a propagation direction of the first plane wave ultrasound beam.

The transmitted second plane wave ultrasound beam may enter the scan target, and the fluid and the tissue in the scan target may disperse and/or reflect this second plane wave ultrasound beam. The probe 1 may receive echoes (referred to herein as second plane wave ultrasound beam echoes) formed by the dispersion and/or reflection of the second plane wave ultrasound beam by the scan target, and convert these echoes into electrical signals. The electrical signals may be processed by multiple units such as the receiving circuit 4 and the beamformer 5, etc., to acquire echo signals corresponding to the transmitted second plane wave ultrasound beams, which are referred to in this present disclosure as second plane wave echo signals.

In step 14, the transmitting circuit 2 may excite the probe 1 to transmit focused ultrasound beams to the scan target. The focused ultrasound beam may enter the scan target and may be focused at a pre-set location (i.e. a focal point) in the scan target. The fluid and the tissue in the scan target may disperse and/or reflect this focused ultrasound beam. The probe 1 may receive echoes (referred to in the present disclosure as focused ultrasound beam echoes) formed by the dispersion and/or reflection the focused ultrasound beam by the scan target, and convert these echoes into electrical signals. The electrical signals may be processed by multiple units such as the receiving circuit 4 and the beamformer 5, etc., to acquire echo signals corresponding to the transmitted focused ultrasound beams, which are referred to herein as focused beam echo signals.

After acquiring the first plane wave echo signals, in step 16, a first velocity component of a target point (for example, a point or a location for which the velocity vector is to be acquired) in the scan target can be acquired using the first plane ultrasound echo signals, which is the first velocity component of the movement velocity of a fluid or a tissue at the target point.

As stated previously, a velocity component in the propagation direction of the ultrasound beam can be acquired by performing Doppler processing on the ultrasound echo signal. Therefore, in the embodiments of the present disclosure, in step 16, a velocity component of movement of the fluid or the tissue at the target point in the scan target in the propagation direction of the first plane wave ultrasound beam can be acquired by performing Doppler processing on first plane wave echo signals, which is referred to herein as a first velocity component of the target point. It can be seen that the first velocity component may be also a vector, the size of the vector can be acquired according to the aforesaid Doppler processing, and the direction of the vector may be the propagation direction of the first plane wave ultrasound beam. The propagation direction of the first plane wave ultrasound beams can be acquired from a steered angle (i.e. the aforesaid first steered angle) of the first plane wave ultrasound beam; however, this first steered angle of the first plane wave ultrasound beam is known.

Likewise, in the embodiments of the present disclosure, in step 16, a velocity component of movement of the fluid or the tissue at the target point in the scan target in the propagation direction of the second plane wave ultrasound beam can also be acquired by performing Doppler processing on second plane wave echo signals, which is referred to herein as a second velocity component of the target point.

Similarly, the second velocity component may be also a vector, the size of the vector can be acquired according to the aforesaid Doppler processing, and the direction of the vector may be the propagation direction of the second plane wave ultrasound beam. The propagation direction of the second plane wave ultrasound beam can be acquired from a steered angle (i.e. the aforesaid second steered angle) of the second plane wave ultrasound beam; however, this second steered angle of the second plane wave ultrasound beam can be known.

After acquiring focused beam echo signals, in step 18, an ultrasound image of at least part of the scan target can be acquired using the focused beam echo signals, i.e. performing corresponding processing on the focused beam echo signals so as to acquire the ultrasound image of at least part of the scan target. From the description stated previously, each focused ultrasound beam may be generally focused at a focal point, and therefore, image data of one or more scan lines of the scan target can be generally acquired using each focused beam echo signal. Here, an image (or image data of the one or more scan lines) of at least part of the scan target acquired using the focused beam echo signal may be a B mode image (or B mode image data), and may also be an ultrasound image (or ultrasound image data) of any other suitable modes. Any suitable methods that could be currently used in the art and could be generally used in the future can be used to acquire the ultrasound image (or ultrasound image data) of at least part of the scan target using the acquired focused beam echo signal, and will not be described again herein.

As stated previously, the first velocity component and the second velocity component of the target point have been acquired in step 16. After acquiring the first velocity component and the second velocity component, in step 20, the velocity vector (referred to herein as the velocity vector of the target point) of the tissue or the fluid at the target point can be acquired at least by combining this first velocity component and this second velocity component by using the principle of vector synthesis.

In the aforesaid embodiments, two velocity components of the target point may be acquired via two kinds of plane wave ultrasound beams propagated in two directions, and then the velocity vector of the target point may be synthesised using at least these two velocity components. Therefore, in the aforesaid embodiments, the aforesaid "target point" can be at a location at an overlapped position of the first plane wave ultrasound beam and the second plane wave ultrasound beam. Moreover, each transmission of focused ultrasound beams may be used to image at least part of the scan target, and the part of the scan target imaged by each transmission of the focused ultrasound beam can contain the aforesaid target location or is at least partially overlapped with the aforesaid target location, and can also be separate from the aforesaid target location. The embodiments of the present disclosure do not limit the part imaged by each transmission of the focused ultrasound beam to being the same as the target location where the plane wave ultrasound beams can be imaged.

After acquiring the velocity vector of the target point and the ultrasound image of at least part of the scan target, in step 22, the velocity vector and the ultrasound image can be displayed. For example, the velocity vector and the ultrasound image can be simultaneously displayed on the display device 8. For example, in the embodiment of the present disclosure, the velocity vector can be displayed on the ultrasound image in a superimposed manner.

In an embodiment of the present disclosure, step 16, step 18 and/or step 20 as stated previously can be executed by the date processor 9 of the ultrasound imaging system. In an embodiment of the present disclosure, the date processor 9 may include the signal processing unit 6 and/or the image processing unit 7, and step 16, step 18 and/or step 20 as stated previously can be executed by the signal processing unit 6 and/or the image processing unit 7.

In the aforesaid embodiments, the first plane wave ultrasound beams and the second plane wave ultrasound beams may be transmitted so as to acquire the first velocity component and the second velocity component of the target point in the scan target, and then the velocity vector at the target point can be acquired by combining at least the first velocity component and the second velocity component. However, in another embodiment of the present disclosure, the transmitting circuit 2 also may excite the probe 1 to transmit a third plane wave ultrasound beam to the scan target. The third plane wave ultrasound beam can be an unfocused plane wave as stated previously, and may have a third steered angle. The third steered angle can be different from the aforesaid first steered angle and second steered angle. That is to say, a propagation direction of the third plane wave ultrasound beam may be actually different from the propagation directions of the first plane wave ultrasound beam and the second plane wave ultrasound beam.

The transmitted third plane wave ultrasound beam may enter the scan target, and the fluid and the tissue in the scan target may disperse and/or reflect this third plane wave ultrasound beam. The probe 1 may receive echoes (referred to in the present disclosure as third plane wave ultrasound beam echoes) formed by the dispersion and/or reflection of the third plane wave ultrasound beam by the scan target, and convert these echoes into electrical signals. The electrical signals may be processed by multiple units such as the receiving circuit 4 and the beamformer 5 etc., to acquire echo signals corresponding to the transmitted third plane wave ultrasound beam, which are referred to herein as third plane wave echo signals.

After acquiring the third plane wave echo signals, similar to the description as stated previously, a velocity component of movement of the fluid or the tissue at the target point in the scan target in the propagation direction of the third plane wave ultrasound beam can also be acquired by performing Doppler processing on third plane wave echo signals, and this velocity component may be referred to herein as a third velocity component of the target point. Therefore, at this point, the third velocity component at the target point can be acquired using the third plane wave echo signals.

The third velocity component may be also a vector, the size of the vector can be acquired according to the aforesaid Doppler processing, and the direction of the vector may be the propagation direction of the third plane wave ultrasound beam. The propagation direction of the third plane wave ultrasound beam can be acquired from a steered angle (i.e. the aforesaid third steered angle) of the third plane wave ultrasound beam; however, this third steered angle of the third plane wave ultrasound beam can be known.

Then, the velocity vector of the target point can be acquired at least by combining the aforesaid first velocity component, the second velocity component and the third velocity component.

Similarly, in the aforesaid embodiments, the aforesaid "target point" can be at a location at an overlapped (or intersection) position of the first plane wave ultrasound beam, the second plane wave ultrasound beam and the third plane wave ultrasound beam. Likewise, the part imaged by each transmission of the focused ultrasound beam can contain the aforesaid target location or is at least partially overlapped with the aforesaid target location, and can also be separate from the aforesaid target location. The embodiments of the present disclosure do not limit the part imaged by each transmission of the focused ultrasound beam to being the same as the target location where the plane wave ultrasound beams are imaged.

In this embodiment, velocity components of the target point in three directions can be acquired using plane wave ultrasound beams in three propagation directions, and then the velocity vector of the target point may be synthesised using these three velocity components. The acquired velocity vector may be higher precision with better stability. It can be easily understood that, in the embodiments of the present disclosure, the plane wave ultrasound beams in more directions can also be transmitted to the target location in the scan target so as to acquire velocity components in more directions, and then the velocity vector of the target point may be synthesised using these velocity components in more directions. Generally, when using the plane wave ultrasound beams in the more directions, the velocity vector finally acquired through combination may have higher precision and better stability.

In an embodiment of the present disclosure, the aforesaid step of acquiring the third velocity component using the third plane wave echo signals and/or the step of acquiring the velocity vector at the target point by combining the first velocity component, the second velocity component and the third velocity component can also be executed by the date processor 9 of the ultrasound imaging system.

Then, in this embodiment, similar to the aforesaid embodiments, the acquired velocity vector and the ultrasound image of at least part of the scan target acquired using the focused ultrasound beams can be displayed on the display device 8. For example, the velocity vectors can be displayed on the ultrasound image in a superimposed manner.

In an embodiment of the present disclosure, the aforesaid first plane wave ultrasound beams, second plane wave ultrasound beams and/or third plane wave ultrasound beams can be emitted multiple times, and echo signals acquired through each transmission are known as a set of echo signals, thereby a plurality of sets of first plane wave echo signals, a plurality of sets of second plane wave echo signals and/or a plurality of sets of third plane wave echo signals can be acquired; and then, a first velocity component, a second velocity component and/or a third velocity component of the target point can be respectively acquired by respectively performing Doppler processing on the plurality of sets of first plane wave echo signals, the plurality of sets of second plane wave echo signals and/or the plurality of sets of third plane wave echo signals.

Moreover, as stated previously, during the transmission of focused ultrasound beams, since the focused ultrasound beam may be focused at a focal point, image data of one or several scan lines of the scan target can only be acquired using the focused beam echo signal acquired through each transmission of the focused ultrasound beam. Therefore, in an embodiment of the present disclosure, the aforesaid focused ultrasound beams can also be emitted multiple times, a set of focused beam echo signals acquired by each transmission may be processed to acquire image data of one or several scan lines of the scan target, and then at least one portion of these focused ultrasound beams can be focused at different focal points; in this way, image data of one or several scan lines of different locations in the scan target can be acquired. Then, the image data of the one or several scan lines acquired in multiple transmissions may be combined to acquire one complete image or at least part of one complete image of the scan target.

Figure 7:
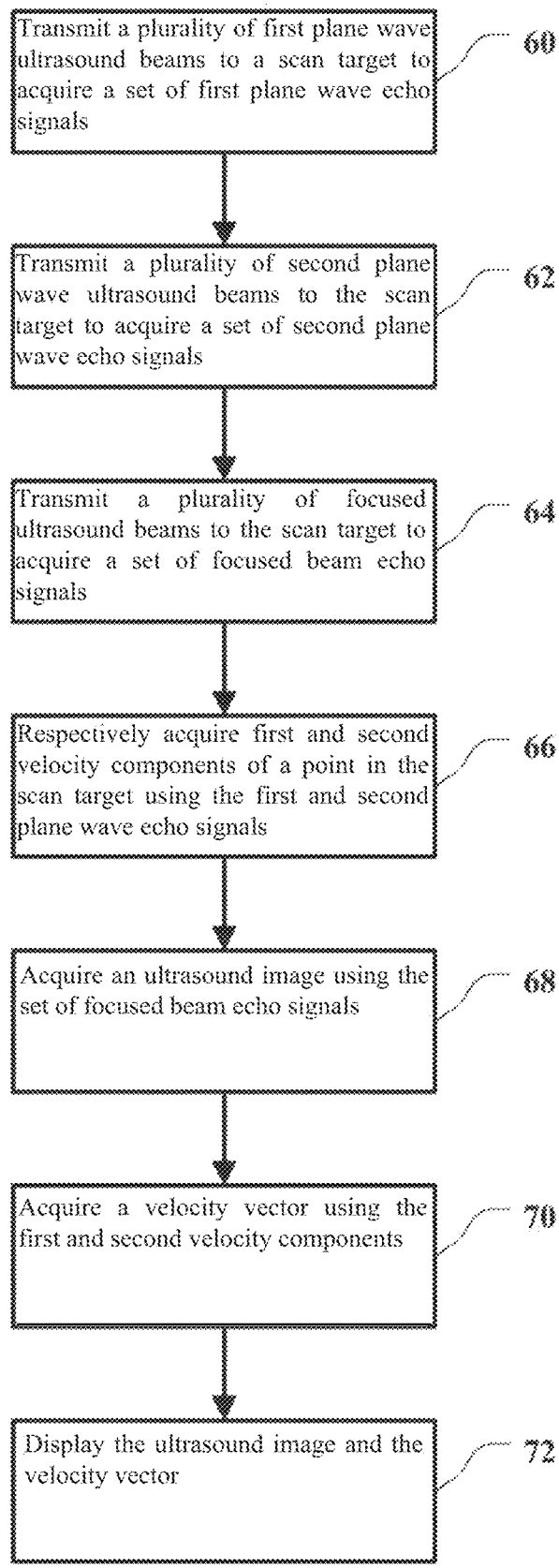
FIG. 7 is a schematic flow diagram of an ultrasound imaging method according to an embodiment of the present disclosure.

Therefore, in another embodiment of the present disclosure, a schematic flow diagram of an ultrasound imaging method can be as shown in FIG. 7. It should be understood that although each step in the flow diagram in FIG. 7 may be displayed in succession as indicated by an arrow, these steps are not necessarily executed in succession in the order indicated by the arrows. Unless expressly described herein, the execution of these steps may be not limited to a strict order, instead, the steps can be executed in another order. In addition, at least some steps in FIG. 7 may include multiple sub-steps or multiple stages. These sub-steps or stages may be not necessarily executed or completed at the same moment, but can be executed at different times, and the order of execution thereof may be also not necessarily in succession, but can be executed in turn or alternately with at least some other steps or sub-steps or stages of other steps.

In the embodiment shown in FIG. 7, in step 60, the transmitting circuit 2 may excite the probe 1 to transmit a plurality of first plane wave ultrasound beams to a scan target (such as a blood vessel or another vessel within which a fluid is flowing in an organism, etc.). The plurality of first plane wave ultrasound beams can be unfocused plane waves as stated previously, and each first plane wave ultrasound beam may have a first steered angle. Each transmitted first plane wave ultrasound beam may enter the scan target, and a fluid and a tissue in the scan target may disperse and/or reflect this first plane wave ultrasound beam. The probe 1 may receive echoes formed by the dispersion and/or reflection of the first plane wave ultrasound beam by the scan target, and convert these echoes into electrical signals. The electrical signals may be processed by multiple units such as the receiving circuit 4 and the beamformer 5, etc., to acquire the first plane wave echo signal. In this embodiment, the plurality of first plane wave ultrasound beams may be transmitted, a set of first plane wave echo signals may be obtained based on each first plane wave ultrasound beam, and therefore, a plurality of sets of first plane wave echo signals can be acquired based on the plurality of first plane wave ultrasound beams.

Similarly, in step 62, the transmitting circuit 2 may excite the probe 1 to transmit a plurality of second plane wave ultrasound beams to a scan target. The second plane wave ultrasound beams can be unfocused plane waves as stated previously, and each second plane wave ultrasound beam may have a second steered angle. The second steered angle can be different from the aforesaid first steered angle. That is to say, a propagation direction of each second plane wave ultrasound beam may be actually different from a propagation direction of each first plane wave ultrasound beam.

The transmitted second plane wave ultrasound beam may enter the scan target, and the fluid and the tissue in the scan target may disperse and/or reflect this second plane wave ultrasound beam. The probe 1 may receive echoes formed by the dispersion and/or reflection of the second plane wave ultrasound beam by the scan target, and convert these echoes into electrical signals. The electrical signals may be processed by multiple units such as the receiving circuit 4 and the beamformer 5 etc., to acquire a second plane wave echo signal. In this embodiment, the plurality of second plane wave ultrasound beams may be transmitted, a set of second plane wave echo signals can be obtained based on each second plane wave ultrasound beam, and therefore, a plurality of sets of second plane wave echo signals can be acquired based on the plurality of second plane wave ultrasound beams.

In step 64, the transmitting circuit 2 may excite the probe 1 to transmit a plurality of focused ultrasound beams to the target location in the scan target. Each of the focused ultrasound beams may enter the scan target and may be focused at a pre-set location (i.e. a focal point) in the scan target. The fluid and the tissue in the scan target may disperse and/or reflect this focused ultrasound beam. The probe 1 may receive echoes formed by the dispersion and/or reflection of the focused ultrasound beam by the scan target, and convert these echoes into electrical signals. The electrical signals may be processed by multiple units such as the receiving circuit 4 and the beamformer 5, etc., to acquire a focused beam echo signal. In this embodiment, the plurality of focused ultrasound beams may be transmitted, a set of focused beam echo signals can be obtained based on each focused ultrasound beam, and therefore, a plurality of sets of focused beam echo signals can be acquired based on the plurality of focused ultrasound beams.

After acquiring the plurality of sets of first plane wave echo signals, in step 66, a first velocity component of the target point can be acquired using the plurality of sets of first plane wave echo signals. In this embodiment, similar to step 16, the first velocity component of the target point can be acquired by performing Doppler processing on the plurality of sets of first plane wave echo signals. The first velocity component may be a vector, the size of the vector can be acquired according to the aforesaid Doppler processing, and the direction of the vector can be the propagation directions of the plurality of first plane wave ultrasound beams.

Likewise, in the embodiments of the present disclosure, in step 66, a second velocity component of the target point in the propagation direction of the plurality of second plane wave ultrasound beams can also be acquired by performing Doppler processing on the plurality of sets of second plane wave echo signals. The second velocity component may be also a vector, the size of the vector can be acquired according to the aforesaid Doppler processing, and the direction of the vector can be the propagation direction of the second plane wave ultrasound beam.

After acquiring the plurality of sets of focused beam echo signals, in step 68, an ultrasound image of at least part of the scan target can be acquired using the plurality of sets of focused beam echo signals, i.e. performing corresponding processing on the focused beam echo signals so as to acquire an ultrasound image of at least part of a scan target. From the description stated previously, each focused ultrasound beam can be generally focused at a focal point, and therefore, image data of one or more scan lines of the scan target can be generally acquired using each focused beam echo signal. In this embodiment, the focused ultrasound beams can be transmitted multiple times, image data of one or several scan lines of the scan target can be acquired by each transmission, and at least one portion of these focused ultrasound beams transmitted multiple times can be focused at different focal points; in this way, image data of one or several scan lines of different locations in the scan target can be acquired. Then, the image data of the one or several scan lines acquired in multiple transmissions may be combined to acquire one complete image or at least part of one complete image of the scan target.

Here, the ultrasound image of at least part of the scan target acquired using the focused beam echo signals may be a B mode image, and may also be an ultrasound image of any other suitable modes. Any suitable methods that are currently used in the art and which could be generally used in the future can be used to acquire the ultrasound image of at least part of the scan target using the plurality of sets of acquired focused beam echo signals, and will not be described again herein.

As stated previously, the first velocity component and the second velocity component of a target point have been acquired in step 66. After acquiring the first velocity component and the second velocity component, in step 70, the velocity vector of the target point can be acquired at least using this first velocity component and this second velocity component by using the principle of vector synthesis.

After acquiring the velocity vector of the point in the scan target and the ultrasound image of at least part of the scan target, in step 72, the velocity vector and the ultrasound image can be displayed. For example, the velocity vector and the ultrasound image can be simultaneously displayed on the display device 8. For example, in the embodiment of the present disclosure, the velocity vector can be displayed on the ultrasound image in a superimposed manner.

In an embodiment of the present disclosure, step 66, step 68 and/or step 70 as stated previously can be executed by the date processor 9 of the ultrasound imaging system.

On the basis of the embodiments shown in FIG. 7, in another embodiment of the present disclosure, the transmitting circuit 2 can also excite the probe 1 to transmit a plurality of third plane wave ultrasound beams to the target location in a scan target. Each of the third plane wave ultrasound beams can be an unfocused plane wave as stated previously, and may have a third steered angle. The third steered angle can be different from the aforesaid first steered angle and second steered angle. That is to say, a propagation direction of each third plane wave ultrasound beam may be actually different from the propagation directions of each first plane wave ultrasound beam and each second plane wave ultrasound beam.

Each transmitted third plane wave ultrasound beam may enter the scan target, and the fluid and the tissue in the scan target may disperse and/or reflect this third plane wave ultrasound beam. The probe 1 may receive echoes formed by the dispersion and/or reflection of the third plane wave ultrasound beam by the scan target, and convert these echoes into electrical signals. The electrical signals may be processed by multiple units such as the receiving circuit 4 and the beamformer 5 etc., to acquire a third plane wave echo signal. In this embodiment, the plurality of third plane wave ultrasound beams may be transmitted, while a set of third plane wave echo signals may be acquired based on each third plane wave ultrasound beam, and therefore, a plurality of sets of third plane wave echo signals can be acquired based on the plurality of third plane wave ultrasound beams.

After acquiring the plurality of sets of third plane wave echo signals, similar to the description stated previously, a third velocity component of the target point in the propagation direction of the third plane wave ultrasound beam can also be acquired by performing Doppler processing on the plurality of sets of third plane wave echo signals.

The third velocity component may be also a vector, the size of the vector can be acquired according to aforesaid Doppler processing, and the direction of the vector can be the propagation direction of the third plane wave ultrasound beam.

Then, the velocity vector at the target point can be acquired at least by combining the aforesaid first velocity component, the second velocity component and the third velocity component.

In an embodiment of the present disclosure, the aforesaid step of acquiring the third velocity component using a plurality of sets of third plane wave echo signals and/or the step of acquiring the velocity vector of the target point by combining the first velocity component, the second velocity component and the third velocity component can also be executed by the date processor 9 of the ultrasound imaging system.

In an embodiment of the present disclosure, on the basis of the embodiments stated previously, at least one portion of the aforesaid plurality of first plane wave ultrasound beams and at least one portion of the aforesaid plurality of second plane wave ultrasound beams can be transmitted alternately.

In an embodiment of the present disclosure, on the basis of the embodiments stated previously, at least one of the aforesaid plurality of focused ultrasound beams may be transmitted between a first plane wave ultrasound beam and a second plane wave ultrasound beam adjacent to each other.

In an embodiment of the present disclosure, on the basis of the embodiments stated previously, at least one portion of the aforesaid plurality of first plane wave ultrasound beams, at least one portion of the aforesaid plurality of second plane wave ultrasound beams and at least one portion of the aforesaid plurality of third plane wave ultrasound beams can be transmitted alternately.

In an embodiment of the present disclosure, on the basis of the embodiments stated previously, at least one of the aforesaid plurality of focused ultrasound beams may be transmitted between a first plane wave ultrasound beam and a second plane wave ultrasound beam adjacent to each other, or transmitted between a first plane wave ultrasound beam and a third plane wave ultrasound beam adjacent to each other, or transmitted between a second plane wave ultrasound beam and a third plane wave ultrasound beam adjacent to each other.

For example, FIGS. 8-12 schematically describe multiple transmission modes of plane wave ultrasound beams and focused ultrasound beams according to some embodiments of the present disclosure. In FIGS. 8-12, thin-line arrows may represent plane wave ultrasound beams, thick arrows may represent focused ultrasound beams, and the order of the arrows may represent the respective orders between the processes of transmitting beams and receiving the corresponding echoes thereof. In the thin-line arrows, the thin-line arrows deflected leftward in the figures may represent first plane wave ultrasound beams, the vertical thin-line arrows may represent second plane wave ultrasound beams, and the thin-line arrows deflected rightward may represent third plane wave ultrasound beams. It can be easily understood that which plane wave ultrasound beam each of the thin-line arrows represents can also be defined in a different manner. For example, the case may also be as follows: the thin-line arrows deflected leftward may represent first plane wave ultrasound beams, the thin-line arrows deflected rightward may represent second plane wave ultrasound beams, and the vertical thin-line arrows may represent third plane wave ultrasound beams, etc.

In addition, the number of the plane wave ultrasound beams and the focused ultrasound beams represented schematically in FIGS. 8-12 is merely exemplary, and is not intended to limit the number of the plane wave ultrasound beams and the focused ultrasound beams actually transmitted to being only the number shown in FIGS. 8-12. Actually, the number of the plane wave ultrasound beams and the focused ultrasound beams can be any suitable number.

Figure 8:
FIGS. 8-12 are schematic diagrams of multiple transmission modes of plane wave ultrasound beams and focused ultrasound beams according to some embodiments of the present disclosure.
Figure 9:
Figure 10:
Figure 11:
Figure 12:

As shown in FIG. 8, an embodiment of the present disclosure can be performed in the following order:
transmitting the first one of the first plane wave ultrasound beams and receiving an echo thereof→
transmitting the first one of the second plane wave ultrasound beams and receiving an echo thereof→
transmitting the first one of the third plane wave ultrasound beams and receiving an echo thereof→
transmitting the first focused ultrasound beam and receiving an echo thereof→
transmitting the second one of the second plane wave ultrasound beams and receiving an echo thereof→
transmitting the second one of the third plane wave ultrasound beams and receiving an echo thereof→
transmitting the second one of the first plane wave ultrasound beams and receiving an echo thereof→
transmitting the third one of the second plane wave ultrasound beams and receiving an echo thereof→ transmitting the third one of the third plane wave ultrasound beams and receiving an echo thereof→
transmitting the third one of the first plane wave ultrasound beams and receiving an echo thereof→
transmitting the second focused ultrasound beam and receiving an echo thereof→
transmitting the fourth one of the third plane wave ultrasound beams and receiving an echo thereof→
transmitting the fourth one of the first plane wave ultrasound beams and receiving an echo thereof→
transmitting the fourth one of the second plane wave ultrasound beams and receiving an echo thereof→
transmitting the fifth one of the third plane wave ultrasound beams and receiving an echo thereof→
transmitting the fifth one of the first plane wave ultrasound beams and receiving an echo thereof→
transmitting the fifth one of the second plane wave ultrasound beams and receiving an echo thereof→
transmitting the third focused ultrasound beam and receiving an echo thereof→
transmitting the sixth one of the first plane wave ultrasound beams and receiving an echo thereof→
. . . .

The above-mentioned process can be performed repeatedly.

It can be seen from FIG. 8 that, in this embodiment, the first plane wave ultrasound beam, the second plane wave ultrasound beam and the third plane wave ultrasound beam can be roughly considered to be a set of plane wave ultrasound beams, and each set of plane wave ultrasound beams may be repeatedly transmitted to receive corresponding echoes, where in certain sets, a certain plane wave ultrasound beam in this set can be replaced by focused ultrasound beams. For example, in FIG. 8, the left-most three plane wave ultrasound beams are taken as a first set of plane wave ultrasound beams, which are sequentially numbered from left to right as a second set, a third set, a fourth set, a fifth set, a sixth set, a seventh set, etc., and so on. It can be seen that a first plane wave ultrasound beam in the second set can be replaced by a first focused ultrasound beam, a second plane wave ultrasound beam in the fourth set can be replaced by a second focused ultrasound beam, a third plane wave ultrasound beam in the sixth set can be replaced by a third focused ultrasound beam, and so on.

When calculating velocity component using plane wave ultrasound beam echo signals, some plane wave ultrasound beams in these sets can be replaced by focused ultrasound beams, so there may not have plane wave echo signals obtained corresponding to the replaced plane wave ultrasound beams in certain sets. At this point, the plane wave echo signals of the replaced plane wave ultrasound beams can be acquired by means of interpolation of one or several former sets of plane wave echo signals of corresponding plane wave ultrasound beams and one or several latter sets of plane wave echo signals of corresponding plane wave ultrasound beam.

For example, in the embodiments of FIG. 8, a first plane wave ultrasound beam in the second set of plane wave ultrasound beams can be replaced by focused ultrasound beams, and therefore, during the calculation of the first velocity component, a first plane wave echo signal of this first plane wave ultrasound beam in the second set can be acquired by means of interpolation of a first plane wave echo signal of a first plane wave ultrasound beam in the first set and a first plane wave echo signal of a first plane wave ultrasound beam in the third set.

In the embodiments of the present disclosure, the plane wave ultrasound beams and the focused ultrasound beams can also be transmitted in another manner, as shown in FIGS. 9-12 for example. The transmission process and significance thereof shown in FIGS. 9-12 can be acquired with reference to the description above for the transmission process in relation to FIG. 8, and will not be described again herein.

One of the objectives of the embodiments of the present disclosure is to provide an ultrasound imaging method and system, which not only enable the acquisition of a velocity vector in real time with high accuracy, but also enable the acquisition of a high quality image.

In the ultrasound imaging method and the ultrasound imaging system thereof provided in the embodiments of the present disclosure, both the plane wave ultrasound beams and the focused ultrasound beams may be used in the imaging process. The plane wave ultrasound beam may be used to acquire the velocity vector, whereby the advantages of the high frame rate of plane wave ultrasound beam imaging may be fully used to meet the requirements for high frame rate when measuring a fluid velocity using ultrasound imaging; while the focused ultrasound beam may be used to acquire the ultrasound image of the scan target, whereby the advantages of a high signal-to-noise ratio of the echo signal, good quality of the acquired ultrasound image and high lateral resolution of the focused ultrasound beam imaging echo signal may be fully used in order to acquire a good image for observation by the user. In this way, not only can the velocity vectors with a high frame rate in real time and with high accuracy be obtained, but ultrasound images (for example, a B mode image) with high quality can also be acquired, whereby at the same time as presenting the velocity vector (for example, the velocity vector of blood flow), organs such as surrounding tissues and vessel walls can still clearly appear on a grey-scale image.

In addition, in these embodiments of the present disclosure, the plane wave ultrasound beams and the focused ultrasound beams may be transmitted alternately over time, i.e. the transmission of the focused ultrasound beams may be dispersed and inserted between the transmissions of the plane wave ultrasound beams. In this way, not only the continuity of the velocity vector can be maintained, but also the synchronism of the velocity vector and the ultrasound image (for example, the B image) can be ensured.

The present disclosure may be described above by means of specific embodiments, but the present disclosure should not be considered to be limited to these specific embodiments. Those skilled in the art should understand that various modifications, equivalent substitutions, and changes, etc., may also be made to the present disclosure without departing from the spirit of the present disclosure, whilst all falling within the scope of protection of the present disclosure. Moreover, the phrase "an embodiment", which appears in multiple places above, represents different embodiments, which can naturally also be combined fully or partially into one embodiment.

The invention claimed is:
1. A method of ultrasound imaging comprising:
transmitting a first set of plane wave ultrasound beams to a scan target including tissue and blood flow, wherein the first set of plane wave ultrasound beams comprises a plane wave ultrasound beam with a first steered angle and a plane wave ultrasound beam with a second steered angle;

transmitting a plurality of focused ultrasound beams to the scan target after the first set of plane wave ultrasound beams;
transmitting a second set of plane wave ultrasound beams to the scan target, wherein the second set of plane wave ultrasound beams comprises a plane wave ultrasound beam with the first steered angle and a plane wave ultrasound beam with the second steered angle, wherein the first and second sets of plane wave ultrasound beams are for measuring a velocity of the blood flow within the tissue, and wherein the focused ultrasound beams are for acquiring an ultrasound image of the scan target;
respectively receiving echoes of each set of plane wave ultrasound beams to acquire a plurality of sets of plane wave echo signals and receiving echoes of the plurality of focused ultrasound beams to acquire a plurality of sets of focused echo signals;
acquiring a velocity vector of a target point in the blood flow using the plurality of sets of plane wave echo signals;
acquiring an ultrasound image of at least part of the tissue using the plurality of sets of focused echo signals; and
displaying the velocity vector and the ultrasound image.

2. The method of claim 1, wherein the step of acquiring a velocity vector of a target point in the blood flow using the plurality of sets of plane wave echo signals comprises:
acquiring, by a data processor, at least a first frame of plane wave echo image data and a second frame of plane wave echo image data using the plurality of sets of plane wave echo signals;
selecting, by the data processor, a tracking area in the first frame of plane wave echo image data, the tracking area containing the target point and being a neighbourhood of the target point or a data block containing the target point;
searching for, by the data processor, a tracking result area containing the target point and having the maximum similarity to the tracking area in the second frame of plane wave echo image data; and
acquiring, by the data processor, the velocity vector of the target point according to the positions of the tracking area and the tracking result area and a time interval between a moment acquiring the first frame of plane wave echo image data and a moment acquiring the second frame of plane wave echo image data.

3. The method of claim 1, wherein the step of acquiring a velocity vector of a target point in the blood flow using the plurality of sets of plane wave echo signals comprises:
acquiring at least two frames of plane wave echo image data using the plurality of sets of plane wave echo signals;
acquiring a first gradient at the target point along a temporal direction using the plane wave echo image data;
acquiring a second gradient at the target point along a propagation direction of the plane wave ultrasound beam using the plane wave echo image data;
acquiring a third gradient at the target point along a direction perpendicular to the propagation direction of the plane wave ultrasound beam using the plane wave echo image data;
acquiring a velocity component of movement of the blood flow at the target point in the propagation direction of the plane wave ultrasound beam acquired by performing Doppler processing on the plurality of sets of plane wave echo signals;

calculating a velocity component of movement of the blood flow at the target point in the direction perpendicular to the propagation direction of the plane wave ultrasound beam based on chain rule using the first gradient, the second gradient, the third gradient and the velocity component of movement of the blood flow at the target point in the propagation direction of the plane wave ultrasound beam; and
acquiring the velocity vector of the target point by combining the velocity component of the movement of the blood flow at the target point in the propagation direction of the plane wave ultrasound beam and the velocity component of the movement of the blood flow at the target point in the direction perpendicular to the propagation direction of the plane wave ultrasound beam.

4. The method of claim 1, wherein the step of acquiring a velocity vector of a target point in the blood flow using the plurality of sets of plane wave echo signals comprises:
acquiring at least two frames of plane wave echo image data using the plurality of sets of plane wave echo signals;
acquiring a first gradient at the target point along a temporal direction using the plane wave echo image data;
acquiring a second gradient at the target point along a propagation direction of the plane wave ultrasound beam using the plane wave echo image data;
acquiring a third gradient at the target point along a direction perpendicular to the propagation direction of the plane wave ultrasound beam using the plane wave echo image data;
calculating a velocity component of movement of the blood flow at the target point in the propagation direction of the plane wave ultrasound beam and a velocity component of movement of the blood flow at the target point in the direction perpendicular to the propagation direction of the plane wave ultrasound beam based on least square method using the first gradient, the second gradient and the third gradient; and
acquiring the velocity vector of the target point by combining the velocity component of the movement of the blood flow at the target point in the propagation direction of the plane wave ultrasound beam and the velocity component of the movement of the blood flow at the target point in the direction perpendicular to the propagation direction of the plane wave ultrasound beam.

5. The method of claim 1, wherein the step of displaying the velocity vector and the ultrasound image comprises:
displaying the velocity vector on the ultrasound image in a superimposed manner.

6. A method of ultrasound imaging method comprising:
transmitting a plurality of first plane wave ultrasound beams to a scan target including tissue, wherein each of the first plane wave ultrasound beams having a first steered angle;
receiving echoes of the plurality of first plane wave ultrasound beams to acquire a plurality of sets of first plane wave echo signals;
transmitting a plurality of second plane wave ultrasound beams to the scan target, wherein each of the second plane wave ultrasound beams having a second steered angle, and wherein the plurality of the first and second plane wave ultrasound beams are for measuring a velocity of the blood flow within the tissue;
receiving echoes of the plurality of second plane wave ultrasound beams to acquire a plurality of sets of second plane wave echo signals;

transmitting a plurality of focused ultrasound beams to the scan target, wherein at least one portion of the plurality of first plane wave ultrasound beams, at least one portion of the plurality of second plane wave ultrasound beams and at least one portion of the plurality of focused ultrasound beams are transmitted alternately;

receiving echoes of the plurality of focused ultrasound beams to acquire a plurality of sets of focused beam echo signals;

acquiring a first velocity component of a target point in the blood flow using the plurality of sets of first plane wave echo signals;

acquiring a second velocity component of the target point using the plurality of sets of second plane wave echo signals;

acquiring an ultrasound image of at least part of the tissue using the plurality of sets of focused beam echo signals; and acquiring a velocity vector of the target point at least using the first velocity component and the second velocity component; and displaying the velocity vector and the ultrasound image.

7. The method of claim 6, further comprising:

transmitting a plurality of third plane wave ultrasound beams to the scan target, wherein each of the third plane wave ultrasound beams having a third steered angle, receiving echoes of the plurality of third plane wave ultrasound beams to acquire a plurality of sets of third plane wave echo signals, and acquiring a third velocity component of the target point using the plurality of sets of third plane wave echo signals, wherein the step of acquiring a velocity vector of the target point at least using the first velocity component and the second velocity component comprises:

acquiring the velocity vector of the target point at least using the first velocity component, the second velocity component and the third velocity component.

8. The method of claim 6, wherein at least one portion of the plurality of first plane wave ultrasound beams and at least one portion of the plurality of second plane wave ultrasound beams are transmitted alternately.

9. The method of claim 8, wherein at least one of the plurality of focused ultrasound beams is transmitted between a first plane wave ultrasound beam and a second plane wave ultrasound beam adjacent to each other.

10. The method of claim 7, wherein at least one portion of the plurality of first plane wave ultrasound beams, at least one portion of the plurality of second plane wave ultrasound beams and at least one portion of the plurality of third plane wave ultrasound beams are transmitted alternately.

11. The method of claim 10, wherein at least one of the plurality of focused ultrasound beams is transmitted between a first plane wave ultrasound beam and a second plane wave ultrasound beam adjacent to each other, or between a first plane wave ultrasound beam and a third plane wave ultrasound beam adjacent to each other, or between a second plane wave ultrasound beam and a third plane wave ultrasound beam adjacent to each other.

12. The method of claim 6, wherein the step of displaying the velocity vector and the ultrasound image comprises:

displaying the velocity vector on the ultrasound image in a superimposed manner.

13. An ultrasound imaging system comprising:

a probe;

a transmitting circuit, the transmitting circuit being configured to:

transmit a first set of plane wave ultrasound beams to a scan target including tissue and blood flow, wherein the first set of plane wave ultrasound beams comprises a plane wave ultrasound beam with a first steered angle and a plane wave ultrasound beam with a second steered angle;

transmit a plurality of focused ultrasound beams to the scan target after the first set of plane wave ultrasound beams;

transmit a second set of plane wave ultrasound beams to the scan target, wherein the second set of plane wave ultrasound beams comprises a plane wave ultrasound beam with the first steered angle and a plane wave ultrasound beam with the second steered angle, wherein the first and second sets of plane wave ultrasound beams are for measuring a velocity of the blood flow within the tissue, and wherein the focused ultrasound beams are for acquiring an ultrasound image of the scan target;

a receiving circuit and a beamformer, the receiving circuit and the beamformer respectively receiving echoes of each set of plane wave ultrasound beams to acquire a plurality of sets of plane wave echo signals and receiving echoes of the plurality of focused ultrasound beams to acquire a plurality of sets of focused echo signals;

a data processor, the data processor acquiring a velocity vector of a target point in the blood flow using the plurality of sets of plane wave echo signals, and acquiring an ultrasound image of at least part of the tissue using the plurality of sets of focused echo signals; and a display device, the display device displaying the velocity vector and the ultrasound image.

14. The system of claim 13, wherein the data processor being configured to:

acquire at least a first frame of plane wave echo image data and a second frame of plane wave echo image data using the plurality of sets of plane wave echo signals;

select a tracking area in the first frame of plane wave echo image data, the tracking area containing the target point and being a neighbourhood of the target point or a data block containing the target point;

search for a tracking result area containing the target point and having the maximum similarity to the tracking area in the second frame of plane wave echo image data; and acquire the velocity vector of the target point according to the positions of the tracking area and the tracking result area and a time interval between a moment acquiring the first frame of plane wave echo image data and a moment acquiring the second frame of plane wave echo image data.

15. The system of claim 13, wherein the data processor being configured to: acquire at least two frames of plane wave echo image data using the plurality of sets of plane wave echo signals;

acquire a first gradient at the target point along a temporal direction using the plane wave echo image data;

acquire a second gradient at the target point along a propagation direction of the plane wave ultrasound beam using the plane wave echo image data;

acquire a third gradient at the target point along a direction perpendicular to the propagation direction of the plane wave ultrasound beam using the plane wave echo image data;

acquire a velocity component of movement of the blood flow at the target point in the propagation direction of the plane wave ultrasound beam acquired by performing Doppler processing on the plurality of sets of plane wave echo signals;

calculate a velocity component of movement of the blood flow at the target point in the direction perpendicular to the propagation direction of the plane wave ultrasound beam based on chain rule using the first gradient, the second gradient, the third gradient and the velocity component of movement of the blood flow at the target point in the propagation direction of the plane wave ultrasound beam; and acquire the velocity vector of the target point by combining the velocity component of the movement of the blood flow at the target point in the propagation direction of the plane wave ultrasound beam and the velocity component of the movement of the blood flow at the target point in the direction perpendicular to the propagation direction of the plane wave ultrasound beam.

16. The system of claim 13, wherein the data processor being configured to:

acquire at least two frames of plane wave echo image data using the plurality of sets of plane wave echo signals;

acquire a first gradient at the target point along a temporal direction using the plane wave echo image data;

acquire a second gradient at the target point along a propagation direction of the plane wave ultrasound beam using the plane wave echo image data;

acquire a third gradient at the target point along a direction perpendicular to the propagation direction of the plane wave ultrasound beam using the plane wave echo image data;

calculate a velocity component of movement of the blood flow at the target point in the propagation direction of the plane wave ultrasound beam and a velocity component of movement of the blood flow at the target point in the direction perpendicular to the propagation direction of the plane wave ultrasound beam based on least square method using the first gradient, the second gradient and the third gradient; and acquire the velocity vector of the target point by combining the velocity component of the movement of the blood flow at the target point in the propagation direction of the plane wave ultrasound beam and the velocity component of the movement of the blood flow at the target point in the direction perpendicular to the propagation direction of the plane wave ultrasound beam.

17. The system of claim 13, wherein the display device displays the velocity vector on the ultrasound image in a superimposed manner.

* * * * *